United States Patent
Banavar et al.

(10) Patent No.: US 12,272,262 B2
(45) Date of Patent: Apr. 8, 2025

(54) PERSONALIZING FOOD RECOMMENDATIONS TO REDUCE GLYCEMIC RESPONSE

(71) Applicant: Viome Life Sciences, Inc., Bellevue, WA (US)

(72) Inventors: Guruduth S. Banavar, Pelham Manor, NY (US); Hal Tily, New York, NY (US); Stephanie Gline, New York, NY (US); Matvey Genkin, New York, NY (US); Vishakh Gopu, Wakefield, RI (US); Eric Patridge, New Rochelle, NY (US); Helen Messier, Cupertino, CA (US); Reza Basseda, Palisades Park, NJ (US); Debra Heald, Calgary (CA); Alla Perlina, San Diego, CA (US); Momchilo Vuyisich, Bothell, WA (US); Tiep Ba Le, Santa Clara, CA (US)

(73) Assignee: Viome Life Sciences, Inc., Bellevue, WA (US)

( * ) Notice: Subject to any disclaimer, the term of this patent is extended or adjusted under 35 U.S.C. 154(b) by 632 days.

(21) Appl. No.: 17/429,920

(22) PCT Filed: Feb. 12, 2020

(86) PCT No.: PCT/US2020/018013
§ 371 (c)(1),
(2) Date: Aug. 10, 2021

(87) PCT Pub. No.: WO2020/168015
PCT Pub. Date: Aug. 20, 2020

(65) Prior Publication Data
US 2022/0130276 A1 Apr. 28, 2022

Related U.S. Application Data

(60) Provisional application No. 62/804,737, filed on Feb. 12, 2019.

(51) Int. Cl.
G09B 19/00 (2006.01)
G06N 20/20 (2019.01)
(Continued)

(52) U.S. Cl.
CPC ......... *G09B 19/0092* (2013.01); *G06N 20/20* (2019.01); *G16H 20/60* (2018.01); *G16H 50/70* (2018.01)

(58) Field of Classification Search
CPC ...... G09B 19/0092; A23L 33/30; G16H 20/60
See application file for complete search history.

(56) References Cited

U.S. PATENT DOCUMENTS

2003/0091964 A1  5/2003  Yeager
2009/0275002 A1  11/2009  Hoggle
(Continued)

FOREIGN PATENT DOCUMENTS

WO   2018160899 A1   9/2018
WO   2019209753 A1   10/2019
(Continued)

OTHER PUBLICATIONS

Breitwieser, Florian, et al. "A review of methods and databases for metagenomic classification and assembly," Briefings in Bioinformatics, vol. 20, Issue 4, Jul. 2019, pp. 1125-1136, doi.org/10.1093/bib/bbx120, Published: Sep. 23, 2017.
(Continued)

*Primary Examiner* — Robert J Utama
*Assistant Examiner* — Correll T French
(74) *Attorney, Agent, or Firm* — Morgan, Lewis & Bockius LLP

(57) ABSTRACT

Provided herein are methods of generating models for predicting the glycemic response of an individual to consumption of a food or meal. The method involves collecting from a plurality of subjects, phenotypic data, ohmic data,
(Continued)

and glycemic response data to foods or meals having a defined macronutrient profile. This data is then used to train a machine learning algorithm to create a model that predicts glycemic response of an individual to a food or meal based on the macro nutrient profile of the food or meal.

17 Claims, 8 Drawing Sheets

(51) Int. Cl.
*G16H 20/60* (2018.01)
*G16H 50/70* (2018.01)

(56) References Cited

U.S. PATENT DOCUMENTS

| | | |
|---|---|---|
| 2011/0053121 A1 | 3/2011 | Heaton |
| 2011/0091842 A1 | 4/2011 | Dugan |
| 2011/0166881 A1 | 7/2011 | Brazzo et al. |
| 2011/0208617 A1 | 8/2011 | Weiland |
| 2013/0216982 A1 | 8/2013 | Bennett et al. |
| 2015/0079551 A1 | 3/2015 | Egan |
| 2015/0294593 A1 | 10/2015 | Schoen et al. |
| 2015/0294594 A1 | 10/2015 | Pacione et al. |
| 2015/0371553 A1 | 12/2015 | Vento |
| 2016/0035248 A1 | 2/2016 | Gibbs |
| 2016/0098942 A1 | 4/2016 | Messier |
| 2016/0140869 A1 | 5/2016 | Kuwahara et al. |
| 2016/0166195 A1 | 6/2016 | Radecka et al. |
| 2016/0232311 A1* | 8/2016 | Segal .................... G06N 20/00 |
| 2016/0253922 A1 | 9/2016 | Kremen et al. |
| 2016/0379520 A1 | 12/2016 | Borel et al. |
| 2017/0128007 A1* | 5/2017 | Hayter .................... G09B 5/02 |
| 2017/0262948 A1 | 9/2017 | Bhatt et al. |
| 2019/0142875 A1 | 5/2019 | Elinav et al. |
| 2019/0251861 A1 | 8/2019 | Wolf et al. |
| 2020/0066181 A1 | 2/2020 | Hadjigeorgiou et al. |
| 2021/0004591 A1 | 1/2021 | Bellaish et al. |
| 2021/0269860 A1 | 9/2021 | Segal |
| 2022/0102000 A1 | 3/2022 | Segal et al. |
| 2022/0335852 A1 | 10/2022 | Banavar et al. |
| 2022/0335853 A1 | 10/2022 | Banavar et al. |

FOREIGN PATENT DOCUMENTS

| | | |
|---|---|---|
| WO | 2020051559 A1 | 3/2020 |
| WO | 2020076874 A1 | 4/2020 |
| WO | 2020168015 A1 | 8/2020 |

OTHER PUBLICATIONS

Gurry, et al., "Predictability and Persistence of Prebiotic Dietary Supplementation in a Healthy Human Cohort", Scientific Reports, Aug. 23, 2018, vol. 8, 12699 (pp. 1-13).
International Search Report and Written Opinion dated Jun. 26, 2020, for PCT application No. PCT/US2020/018013, 19 pages.
Mendes-Soares, et al., "Assessment of a Personalized Approach to Predicting Postprandial Glycemic Responses to Food Among Individuals Without Diabetes", JAMA Network Open, Feb. 8, 2019, vol. 2, No. 2, e188102 (pp. 1-13).
Zeevi, et al., "Personalized Nutrition by Prediction of Glycemic Responses", Cell, Nov. 19, 2015, vol. 163, No. 5 (pp. 1079-1094).
Korem, T. et al. Bread affects clinical parameters and induces gut microbiome-associated personal glycemic responses, Cell Metabolism, vol. 25, No. 6, Jun. 1, 2017; pp. 1243-1253.
Lee et al. "Metaproteomic analysis of human gut microbiota: where are we heading?", Journal of Biomedical Science, vol. 24, Jun. 12, 2017, pp. 1-8, XP055700633.
Shi, Yanmei et al. Integrated metratranscriptomic and metagenomic analyses of stratified microbial assemblages in the open ocean, The ISME Journal (2011) 5, 999-1013 (Supplemental Materials).
Supplementary European Search Report for EP20755298 dated Jan. 9, 2023; date of completion Sep. 23, 2022, 22 pages.
Supplementary Partial European Search Report for EP20755298 dated Oct. 5, 2022, 24 pages.
US Office Action—Non-Final Rejection for U.S. Appl. No. 17/850,818 dated Dec. 20, 2022, 10 pages [Co-Owned].
US, Office Action for U.S. Appl. No. 17/855,666 dated Jan. 30, 2023, 19 pages [Co-Owned].

* cited by examiner

PERSONALIZING FOOD RECOMMENDATIONS TO REDUCE GLYCEMIC RESPONSE

REFERENCE TO RELATED APPLICATIONS

This application claims the benefit of the priority date of U.S. provisional application 62/804,737, filed Feb. 12, 2019, the contents of which are incorporated herein in their entirety.

STATEMENT AS TO FEDERALLY SPONSORED RESEARCH

None.

BACKGROUND

Glycemic response refers to the effect that a food or meal has on blood glucose levels after consumption. Typically, blood glucose first increases and then decreases after consumption of food. Blood glucose levels are regulated, at least in part, by insulin.

Glycemic index is one measure used to predict the glycemic response to consumption of food. However, the glycemic response of different individuals to the same food varies. The glycemic index of a food does not take into consideration individual differences. Methods of predicting glycemic response to a food by an individual are described in, for example, D. Zeevi et al., "Personalized Nutrition by Prediction of Glycemic Responses," Cell Vol. 163, Issue 5, Nov. 19, 2015.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

SUMMARY

Figure 1:
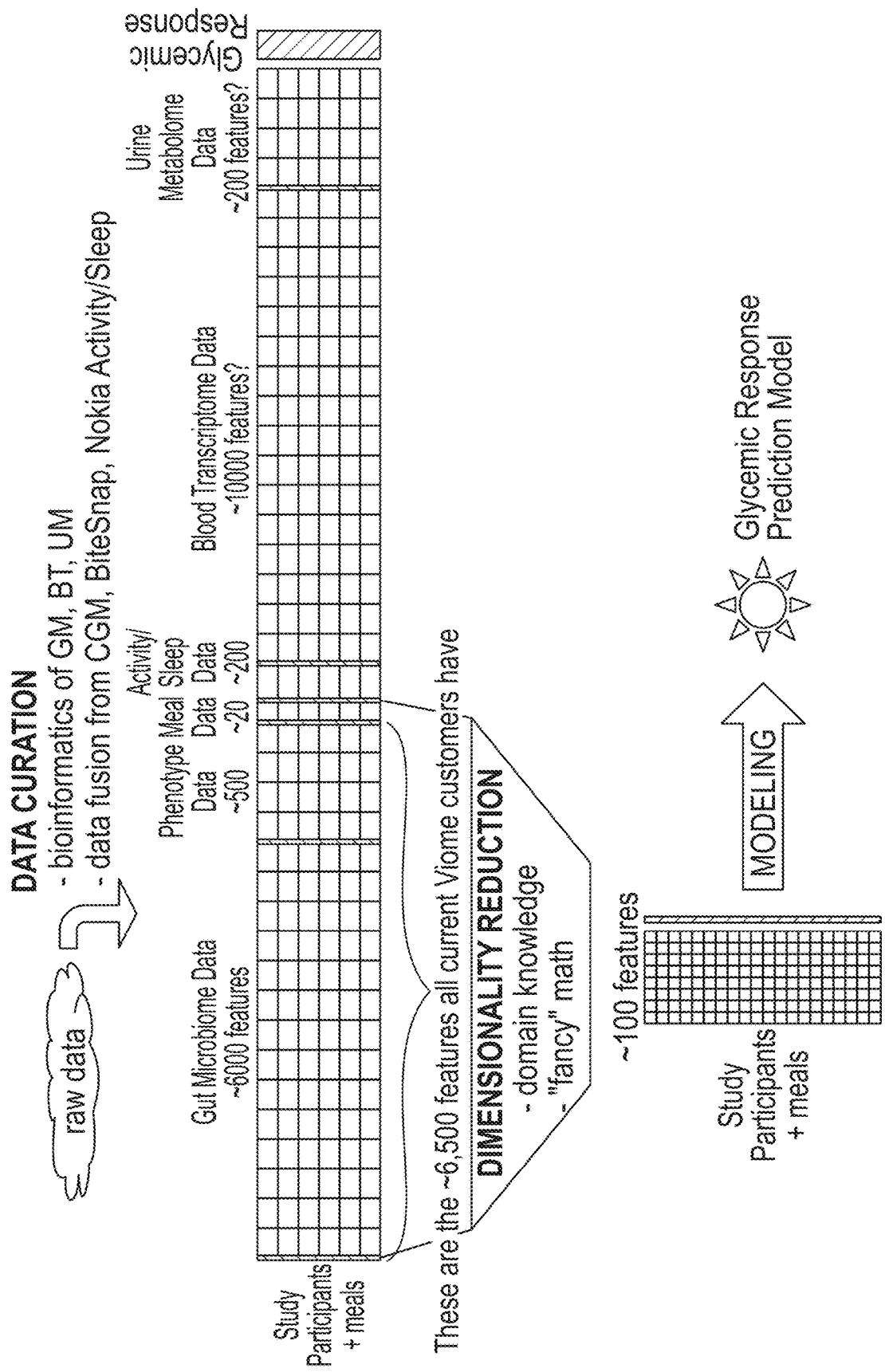
FIG. 1 shows a schema for building a model to predict an individual's glycemic response to a food.

In one aspect, provided herein is a method comprising: a) determining phenotype information about a plurality of phenotypic traits of each of one or a plurality of subjects; b) sequencing nucleic acids from a microbiome sample from each of the subjects to produce nucleic acid sequence information; and c) for each of a plurality of foods, predicting glycemic response to consumption of the food by each of the subjects, based on the phenotype information and the nucleic acid sequence information. In one embodiment, the method further comprises: d) translating the predicted glycemic responses into recommendations about relative or actual amounts of each food to include in a diet of each of the subjects. In another embodiment, the method further comprises: d) for each of a plurality of foods, predicting an impact on one or a plurality of biological conditions experienced by each subject, wherein predicting impact uses information about: (i) the effect of predicted glycemic response on the biological conditions; (ii) the effect of micronutrients in each food on the microbiome of the subject; and (iii) the effect of the microbiome on the biological conditions.

In another aspect, provided herein is a method of generating a glycemic response prediction model comprising: a) providing a dataset that comprises, for each of a plurality of subjects, data including: (i) omic data from the subject, (e.g., data about a microbiome of the subject); (ii) phenotypic data for a plurality of different phenotypic traits for the subject; (iii) meal data for each of a plurality of meals consumed by the subject, including a macronutrient profile for each meal; and (iv) glycemic response data for each subject indicating glycemic response by the subject to each of meals consumed; and b) training a learning algorithm to generate a model that infers a subject's glycemic response to a food or meal based on the subject's profile and the food or meal's macronutrient profile. In another embodiment the omic data comprise one or a plurality of data selected from genomic data, epigenomic data, transcriptomic data RNA, proteomic data, metabolomic data, lipidomic data, glycomic data, immunomic data, phenomic data and exposomic data. In another embodiment the omic data are sourced from a biological sample from the subject selected from stool, blood or urine. In another embodiment the dataset comprises transcriptome data from a stool microbiome. In another embodiment the dataset comprises blood transcriptome data. In another embodiment the dataset comprises urine metabolome data. In another embodiment either or both of activity and sleet data for each subject. In another embodiment providing omic data from the subject comprises sequencing nucleic acid molecules from a sample provided from the subject. In another embodiment providing phenotypic data comprises providing a questionnaire to the subject and receiving from the subject answers to questions on the questionnaire. In another embodiment providing meal data comprises providing a food ontology comprising a macronutrient profile for each food in the food ontology. In another embodiment providing glycemic response data comprises providing each subject with one or a plurality of meals for consumption and, optionally, a schedule for consumption of the meals. In another embodiment providing glycemic response data comprises monitoring blood glucose levels in each subject during and after consumption of a meal. In another embodiment the omic data is abstracted to reflect one or more of: (A) microbiome taxa quantity data for a plurality of microbes in a microbiome of the subject; (B) gene expression data on gene expression (e.g., individual genes or gene orthologs across taxa) for each of a plurality of genes in a microbiome of the subject; and (C) functional activity data on one or a plurality of different biological condition dimensions; and functional activities (e.g., biochemical pathway activity, taxa group activity, or integrative functional activity). In another embodiment the phenotypic traits include one or more of: age, waist-to-hip ratio, weight, body mass index, height, waist size and hip size, ethnicity, place of birth, work environment, food habits and preferences, smoking habits, drinking habits, drug use, activity levels and sleep levels. In another embodiment the macronutrient profile for each meal includes protein content, fat content, carbohydrate content and fiber content. In another embodiment each meal is classified into a meal type, and each meal type is characterized by a different macronutrient profile. In another embodiment the plurality of different meal types is at least any of 10, 20, 30, 40, 50, 60, 70, 80, 90, 100. In another embodiment the glycemic response is classified into a discrete or continuous range. In another embodiment the glycemic response is classified into a category within a set of discrete categories, where in the discrete categories are hierarchically arranged from least to greatest glycemic response. In another embodiment the set comprises two discrete categories, including a lower glycemic response and a higher glycemic response. In another embodiment the set comprises any of 3, 4, 5, 6, 7, 8, 9 or 10 discrete categories. In another embodiment the glycemic response is classified as a number, a degree, a level, a range or bucket. In another embodiment the classification of the glycemic response is based on the shape of a curve of glycemic response over a time period that includes during and after meal consumption. In another embodiment the number of subjects is at least any of 50, 100, 250, 500, 750 or 1000. In another embodiment the plurality of meals consumed is at least any of 500, 1000, 5000, or 10,000.

In another aspect, provided herein is a method of inferring a glycemic response by a subject to each of a plurality of foods, the method comprising: a) providing a dataset comprising: (i) a subject profile comprising: (1) meta-transcriptomic data from a subject (e.g., data from the subject's gut microbiome); and (2) phenotypic data for a plurality of different phenotypic traits for the subject; (ii) food data for each of a plurality of foods, including a macronutrient profile for each food; and b) executing a model of claim 4 on the dataset to infer a glycemic response by the subject to each of the foods. In one embodiment the inferred glycemic response includes a "high" response and a "low" response. In another embodiment the method further comprises: c) communicating to the subject a recommendation with respect to each of the foods, where in the recommendation classifies a food inferred to produce a "low" glycemic response as healthier to consume and classifies a food inferred to produce a "high" glycemic response as less healthy for the subject to consume.

In another aspect, provided herein is a method of assigning each of one or more foods to a personalized desirability hierarchy, the method comprising: a) providing a dataset comprising: (1) data on a state of one or more biological conditions for a subject; (2) data on microbiome taxa profile and microbiome gene expression profile for the subject; (3) food data for each of a plurality of foods, including: (i) data classifying each food according the predicted glycemic response of the subject to the food; (ii) a macronutrient profile for each food; and (iii) a micronutrient profile for each food; b) predicting, based on each food's macronutrient profile and micronutrient profile, the effect on the food on each of the one or more biological conditions in the subject; and c) up-ranking, down-ranking, or leaving unchanged the classification of each food based on whether the food is predicted to improves, worsens or does not affect the one or more biological conditions in the subject. In one embodiment the biological conditions are selected from the biological conditions of Table 3. In another embodiment the state of the biological condition indicates whether the biological condition is present or absent. In another embodiment the state of the biological condition indicates a stage or degree of the biological condition. In another embodiment the microbiome taxa profile indicates relative amounts of microbes in each of a plurality of taxa. In another embodiment the microbiome gene expression profile comprises expression levels of a plurality of microbial genes or activities of functional orthologs. In another embodiment the glycemic response is given as a binary of higher response or lower response. In another embodiment the food data indicates increased desirability to the subject of consuming a food as an inverse function of glycemic response. In another embodiment the data classifying each food is determined by a method as disclosed herein. In another embodiment the plurality of foods is at least any of 10, 25, 50, 75, 100, 150, 200 or 400. In another embodiment a plurality of the foods is selected from Table 2. In another embodiment the macronutrient profile includes relative amounts of each of protein, carbohydrate, fat and fiber. In another embodiment the micronutrient profile comprises quantitative measures of a plurality of micronutrients selected from table 4. In another embodiment the effect of a food on a biological condition indicates exacerbating the condition, improving the condition or having no effect on the condition. In another embodiment the effect of the food on biological condition is indicated on an analog or stepwise scale from worst effect to best effect. In another embodiment up-ranking and down-ranking classifications produces a scale indicating desirability to the subject of consuming a food from most desirable to least desirable. In another embodiment the scale comprises 3, 4, 5, 6, 7, 8, 9 or 10 categories. In another embodiment the scale comprises four hierarchical categories, ranked from most predicted to improve subject biological to most predicted to worsen subject biological.

In another aspect, provided herein is a method comprising: a) providing a cohort of subjects; b) providing each subject in the cohort with questions about the subject's phenotype and receiving, from each subject, responses to the questions; c) providing each subject in the cohort with a kit for collecting a gut microbiome sample from the subject; receiving, from each subject, a kit comprising the gut microbiome sample; and determining omic data from each biological sample from each subject; d) providing each subject one or a plurality of meals to be consumed, each meal characterized by a macronutrient and, optionally, a micronutrient profile; and recording from each subject blood glucose levels including a span of time beginning before consumption of each of the one or more meal to at least any of 60 minutes, 70 minutes, 80 minutes, 90 minutes, 100 minutes, 110 minutes, 120 minutes, 130 minutes, 140 minutes, 150 minutes, 160 minutes, 170 minutes, or 180 minutes after consumption of the meal. In another embodiment the method further comprises providing each subject with a kit for collecting a blood sample from the subject; receiving, from each subject, a kit comprising blood from the subject; and determining blood transcriptome data from a sample. In another embodiment the method further comprises providing each subject with a kit for collecting a urine sample from the subject; receiving, from each subject, a kit comprising urine from the subject; and determining urine metabolome data from a sample. In another embodiment the method further comprises: e) providing a training dataset comprising data obtained at operations (b), (c) and (d) or derived from such data; and f) training a learning algorithm on the training dataset to develop a model that predicts glycemic response of an individual to consumption of food based on the food's macronutrient profile.

In another aspect, provided herein is a method comprising: a) selecting a subject for whom: (i) one or a plurality of foods is classified into a lowest predicted glycemic response category among a plurality of predicted glycemic response categories (e.g., classified as a superfood), wherein the prediction takes into account phenotypic and omic data about the subject; or (ii) one or a plurality of foods is classified into a highest predicted glycemic response category among a plurality of predicted glycemic response categories (e.g., classified as an avoid food), wherein the prediction takes into account phenotypic and omic data about the subject; and b) over a period of at least any of one day, one week, one month or one year, (i) increasing the amount of one or a plurality of the foods classified into the lowest predicted glycemic response category in the diet of the subject compared with a time prior to the period or (ii) decreasing the amount of one or a plurality of the foods classified into the highest predicted glycemic response category in the diet of the subject compared with a time prior to the period. In one embodiment the method comprises both: (i) increasing the amount of one or a plurality of the foods classified into the lowest predicted glycemic response category in the diet of the subject and (ii) decreasing the amount of one or a plurality of the foods classified into the highest predicted glycemic response category in the diet of the subject. In another embodiment, for the subject: (i) one or a plurality of foods is classified into a predicted glycemic response category below the average category but above the lowest category (e.g., classified as an enjoy food), wherein the prediction takes into account phenotypic and omic data about the subject; or (ii) one or a plurality of foods is classified into a predicted glycemic response category above the average category but below the highest category (e.g., classified as a minimize food), wherein the prediction takes into account phenotypic and omic data about the subject; and the method further comprises: c) over a period of at least any of one day, one week, one month or one year, (i) maintaining or increasing the amount of one or a plurality of the foods classified in the below average category in the diet of the subject or (ii) maintaining or decreasing the amount of one or a plurality of the foods classified in the above average category in the diet of the subject. In one embodiment the method further comprises: after selecting, determining amounts of one or more foods in the diet of a subject consumed over a period of at least any of one meal period, one day, one week or one month. In another embodiment one or more biological conditions in the subject is improved.

In another aspect, provided herein is a method comprising: a) for each of a plurality of customers, assigning a rank in a food consumption hierarchy to each of a plurality of foods, to create a ranked food ontology; b) communicating over the Internet, to each of the plurality of customers, the availability of a ranked food ontology personalized to the customer; c) upon receiving a positive response from a customer to the communication, displaying the ranked food ontology personalized to the customer on a page of a website; or communicating to the customer, over the Internet, the ranked food ontology personalized to the customer.

In another aspect provided herein is a system comprising: (a) a computer comprising: (i) a processor; (ii) a memory, coupled to the processor, the memory storing a module comprising: (1) omic data from the subject, including data about a microbiome of the subject and phenotypic data for a plurality of different phenotypic traits for the subject; (2) a food ontology comprising, for a plurality of foods, a macronutrient profile and (iii) a classification rule which, based on the data and food ontology, predicts a glycemic response by the subject to the food and (iv) computer executable instructions for implementing the classification rule on the data.

In another aspect provided herein is a computer readable medium in tangible, non-transitory form comprising machine-executable code that, upon execution by a computer processor, implements a classification rule generated by a method as described herein to predict glycemic response to a food.

DETAILED DESCRIPTION

I. Introduction

Methods of making personalized food, supplement and/or ingredient (sometimes collectively referred to as "food items" or "items") recommendations (herein, "food recommendations") for a subject are described in International Patent application PCT/US 2019/055270, filed, Oct. 8, 2019 (Banavar et al., "Methods for and Compositions for Determining Food Item Recommendations"). The food recommendations provide a beneficial ranking of each food or supplement for the subject based on biological conditions present in the subject and, optionally, based on the subject's predicted glycemic response to the food and/or to the subject's sensitivity to the food. The final recommendation classifies the food according to its effect on the biological conditions, collectively. Rankings are typically hierarchical, from least to most beneficial for the subject to consume. In one model, there are four rankings, including two negative rankings and two positive rankings (or two negative rankings, a neutral ranking and a positive ranking).

Omic information is collected for an individual. This can include Phenomic and Metatranscriptomic data. Analysis of phenomic data can indicate the presence of phenotypic conditions. Bioinformatics can be used to transform metatranscriptomic data into functional activity scores. Functional activity scores that are determined to be outside a reference range indicate the presence of a functional activity condition. Based on phenotypic conditions and functional activity conditions in the subject, a knowledgebase of foods and conditions is accessed. In addition, subject glycemic response to foods and subject food sensitivities also are determined. A computerized recommendation engine then analyses item desirability rankings for all conditions present in the subject and, optionally, the subject's glycemic response to the item and any subject sensitivity to the item. Using logic, the recommendation engine determines an overall, or final recommendation (Food Recommendation) concerning the food items for the subject.

Biological conditions in a subject include any detectable condition, including, without limitation, phenotypic conditions and functional activity conditions. Phenotypic conditions are based on outward phenotype and subjective responses by the subject, obtained, for example by questionnaire. Functional activity conditions are conditions in which a functional activity score for a functional category are determined to be outside a reference range, e.g., suboptimal. Determination of a functional activity condition can be based on biochemical information collected from the subject. Biochemical data can include data from the subject's microbiome, in particular, from the transcriptome of the microbiome. Transcriptome data can be divided into two parts, biochemical pathway activity data and microbial taxa activity data. In other embodiments, biochemical data can include information from the human transcriptome. Biochemical pathway activity data indicates the activity level of various biochemical pathways in the microbes. Taxa activity data indicates the quantity of various active taxa in the gut microbiome, based on their activity levels, which can be measured, for example, as a function of amounts of transcripts measured for the particular taxonomic category. These data are, in turn, analyzed to provide a functional activity score to various higher-level functional activities in the subject that involve a plurality of pathways and taxa, such as inflammatory activity.

Predicted glycemic response to a food by a subject also can be calculated based on changes in blood sugar levels by a subject after consumption of a food or supplement, e.g., as described herein.

Sensitivity of a subject to a food or supplement, e.g., allergy, ("food sensitivity") also can be determined by self-reporting from the subject or by testing, e.g., by skin testing.

The food recommendation engine makes use of a food database. The food database includes a table of foods and supplements. For each biological condition, each food or supplement is ranked (e.g., given a recommendation), according the effect consumption of the food or supplement has on the biological condition (e.g., a positive effect=ameliorates the condition, or a negative effect=worsens the condition). Again, rankings can be provided as a number from low to high, such as 1-4, or by a descriptor, such as "avoid" or "indulge".

Effect of a food item on a subject (that is, beneficial or detrimental effect) (which is reported as a food recommendation) is a function of the collective rankings of the food item on each biological condition that the subject has, as optionally modified by glycemic response and food sensitivity data. Accordingly, for a given subject, rankings of a given food on biological conditions present in the subject, optionally, as well as predicted glycemic response and/or food sensitivity, are used to generate the overall recommendation for the food for the subject. Various functions to generate the overall recommendation can be used. For example, the function could make hierarchical recommendations, in which a food or supplement ranked at a certain level for any biological condition trumps all other rankings for the condition. In one such a function, the presence of a single most negative rank (e.g., "avoid") for any present biological condition would give the food a most negative ("avoid") recommendation. If no food has a most negative rank for any condition present, the presence of a single less negative rank (e.g., "minimize") for any present biological condition would give the food a less negative (e.g., somewhat negative) ("minimize") recommendation. If no food has a most negative or less negative rank for any condition present, the presence of a single most positive rank (e.g., "superfood" or "indulge") for any present biological condition would give the food a most positive ("superfood") recommendation. If no food has any of the aforementioned ranks, a neutral or mildly positive rank (e.g., "enjoy") is assigned to the food for the subject. These rankings can be informed by predicted glycemic response and/or food sensitivity. For example, a high glycemic response (which is a negative response) would cap the recommendation to no better than a negative or less negative ranking, while a low glycemic response (which is a positive response) would not alter the recommendation based on condition ranking, or would increase the ranking by a rank. Similarly, presence of a sensitivity to a food could result in a veto, automatically ranking the food at the least beneficial level.

Disclosed herein are methods of generating models that predict the glycemic response of a subject to a food. Also disclosed herein are methods of personalizing food recommendations for a subject by classifying the predicted glycemic response of a subject to food. Such methods involve executing the models generated on one or more foods in a food ontology. The recommendations will classify foods on a scale from least beneficial (predicted to produce a relatively higher glycemic response) to most beneficial (predicted to produce a relatively lower glycemic response). Recommendations so produced can be further refined to reflect predicted effect of the food on one or more biological conditions experienced by the subject. Refining or reclassifying foods can also include information about subject's food sensitivity.

Referring to FIG. 1, data are collected from a plurality of study participants, each of whom has consumed one or more foods/meals over the course of the study. Raw data used to build a training dataset can include various kinds of omic data such as gut microbiome genomic or transcriptomic data, blood transcriptomic data and/or urine metabolism of data. Such data can be abstracted into features that describe types and amounts of microbes in a subject's microbiome as well as gene expression levels and/or activity of biochemical pathways. Also included in the dataset are phenotype data about each individual subject. Such data can be abstracted from responses by subjects to questionnaires. Meal data for each subject can include data about each meal consumed by a subject during the study. Meal data can include macronutrient and micronutrient information about each meal/food as well as the time of consumption. The dataset can also include activity/sleep data indicating amount and/or quality of sleep, timing of sleep, amount and/or intensity of physical activity and its timing. Glycemic response data can include raw glycemic response data that provides a quantitative measure of blood glucose levels in response to consumption of a meal. Such data can be abstracted to classify the glycemic response. Classifications can be discreet (e.g., high or low, or on a numeric scale) or continuous (e.g., on a continuous scale). In some cases, the dimensionality of the data can be reduced to make it more tractable for a learning algorithm. A machine learning algorithm can be trained on the dataset to generate one or more models that predict the glycemic response of an individual to a food based on the food's macronutrient profile, the subject's phenotypic data and omic data from the subject. A macronutrient profile can include absolute or relative amounts of each of a plurality of macronutrients in a food or meal, on, for example, a mass or calorie basis.

A. Data Sets

Methods of generating models to predict glycemic response can involve providing a training dataset on which a machine learning algorithm can be trained to develop one or more models to predict glycemic response. The training dataset will include data on a plurality of subjects. Data on each subject includes (1) phenotypic data about the subject, (2) omic data from one or more sources about the subject, (3) meal data including macronutrient content about one or more meals consumed by each subject and (4) glycemic response data indicating the glycemic response by a subject to the consumption of a meal.

B. Model Generation and Predicting Glycemic Response

Learning algorithms are trained on the training dataset to generate models that predict the glycemic response of an individual to the consumption of a food of given macronutrient content based on phenotypic data and omic data from the subject. Predicted glycemic responses can be translated into recommendations to the subject about consumption of the food. Subjects can commence a diet reflecting the food recommendations, wherein foods predicted to be more beneficial are consumed in higher quantities than foods predicted to be less beneficial.

C. Contribution to Food Recommendations

Where biological condition states of a subject are known or predicted, food classification can be further refined, e.g., by upgrading or downgrading a food consumption recommendation. Such refining will take into account the impact of the predicted glycemic response on the one or more biological conditions, as well as the impact of the food's micronutrient content on the subject's microbiome and the impact of the subject's microbiome or predicted changes in it to the state of the biological condition.

In a further refinement, foods can be reclassified based on food sensitivity attribute of a subject. For example, a food to which a subject is sensitive can be downgraded in its consumption recommendation.

II. Data Sets

A. Subject Data

In building or executing a model to predict the glycemic response of an individual subject to a food, databases are provided that include information about one or a plurality of subjects. The data can exist in a hierarchy from raw data, at the lowest levels, to data organized at higher levels of abstraction, such as taxonomic information, gene or biochemical pathway activity information and, at a higher level, predicted states of one or more biological conditions.

Raw data can include multi-omic information from a subject and/or a subject's microbiome. This can include, for example, genomic (e.g., genomic DNA sequences), epigenomic (e.g., methylation patterns on DNA), transcriptomic (e.g., sequences of transcribing RNA, in particular, mRNA), proteomic (e.g., identities and/or sequences of proteins in a sample), metabolomic (e.g., chemical products of metabolism), lipidomic (e.g., identity of lipids in a population), glycomic (e.g., information about glycosylation patterns), immunomic (e.g., identity and relative amounts of immune cells or immunoglobulin sequences), phenomic (e.g., information about phenotypic expression) and exposomic (e.g., environmental conditions to which an individual is or has been subject) information.

At a more abstract level, data can include information about microbial taxa about the subject's microbiome. This can include relative amounts of different microbes and add various taxonomic levels. Data can also include information about the activity of various biochemical pathways in the subject. Such data can be derived from the KO (KEGG Orthology) databases or developed by users. The KO databases include, among other things, genomic information, chemical information and systems information such as biological pathway maps.

At a still higher level of abstraction the database can include health scores for a variety of biological conditions that are derivable from the underlying data. Methods for determining health scores are described, for example, in International Patent Application WO 2019/209753, published Oct. 31, 2019 ("Systems And Methods For Inferring Scores For Health Metrics").

A measurement of a variable, such as a phenotypic trait or a functional activity, can be any combination of numbers and words. A measure can be any scale, including nominal (e.g., name or category), ordinal (e.g., hierarchical order of categories), interval (distance between members of an order), ratio (interval compared to a meaningful "0"), or a cardinal number measurement that counts the number of things in a set. Measurements of a variable on a nominal scale indicate a name or category, such a "healthy" or "unhealthy", "old" or "young", "form 1" or "form 2", "subject 1 . . . subject n," etc. Measurements of a variable on an ordinal scale produce a ranking, such as "first", "second", "third"; or order from most to least. Measurements on a ratio scale include, for example, any measure on a pre-defined scale, such as number of molecules, weight, activity level, signal strength, concentration, age, etc., as well as statistical measurements such as frequency, mean, median, standard deviation, or quantile. Measurements on a ratio scale can be relative amounts or normalized measures.

Values for features in the dataset can be quantitative measures of the feature or descriptive terms. Quantitative measures can be given as a discrete or continuous range. Examples of quantitative measures include a number, a degree, a level, a range or bucket. A number can be a number on a scale, for example 1-10. Alternatively, the score can embrace a range. For example, ranges can be high, medium and low; severe, moderate and mild; or actionable and non-actionable. Buckets can comprise discrete numerals, such as 1-3, 4-6 and 7-10.

1. Phenotype Data

Methods and compositions herein can utilize phenotype information for an individual. Any suitable method of determining phenotype information for the individual may be used. Exemplary methods include examination of physical or medical records, one or more interviews with the individual and/or others, examination of the individual, and use of questionnaires.

In certain embodiments, one or more questionnaires are used, where responses to the one or more questionnaires for the individual are used to partially or completely determine phenotype information for the individual, in particular as related to biological conditions, for example biological conditions in an overall set of conditions. The questionnaire or questionnaires may include any suitable number of queries, for example, at least 5, 10, 15, 20, 25, 30, 35, 40, 45, 50, 55, 60, 65, 70, or over 70 questions. Responses to questions can be open-ended (e.g., the individual may provide a written response to a question without limit to content of the response, such as a written answer to a question such as "What are your health goals?"), questions with specific answers (e.g., "what medications do you take," "what is your hip circumference in inches" and the like) or questions where the answer can be selected from a limited number of options, or a combination. Limited option questions include yes/no questions, true/false questions, questions that require selection of one or more response from a limited number of responses, which can be non-numerical responses (e.g., "what is your ethnicity," with responses limited to "American Indian or Alaskan Native," "Southeast Asian," "South Asian," "Asian," "Black or African American," "Native Hawaiian or other Pacific Islander," "Caucasian/White," "Hispanic or Latino," or "Other") or numerical responses (e.g., "How many cups of coffee do you drink each day," with responses limited to 0, 1, 2, 3, 4, 5, 6, 7, 8, 9, or 10+; or "how often have you been bothered by a certain symptom (such as headache, or fatigue, or pain or aches in joints, etc.) in the past four weeks," with the answers limited to "none," "a little," or "a lot," etc.), or any other suitable question type that provides information useful in determining a biological condition.

In another embodiment the phenotypic data providing human phenotype features in the first data set comprises collecting data on objectively and/or subjectively measurable traits for each subject. In another embodiment the phenotypic traits include one or more of: age, sex, weight, blood type, headaches, faintness, dizziness, insomnia, watery or itchy eyes, swollen, red or sticky eyelids, bags or dark circles under eyes, blurred or tunnel vision, not including near or far-sightedness, itchy ears, earaches, ear infections, drainage from ear, ringing in ears, hearing loss, stuffy nose, sinus problems, hay fever, sneezing attacks, excessive mucus formation, chronic coughing, gagging, need to clear throat, sore throat, hoarseness, loss of voice, swollen or discolored tongue, gums or lips, canker sores, acne, hives, rashes, dry skin, hair loss, flushing, hot flashes, excessive sweating, irregular or skipped heartbeat, rapid or pounding heartbeat, chest pain, chest congestion, asthma, bronchitis, shortness of breath, difficulty breathing, bloated feeling, nausea, vomiting, diarrhea, constipation, belching, passing gas, heartburn, intestinal/stomach pain, pain or aches in joints, arthritis, stiffness or limitation of movement, pain or aches in muscles, feeling of weakness or tiredness, binge eating/drinking, craving certain foods, excessive weight, compulsive eating, water retention, underweight, fatigue, sluggishness, apathy, lethargy, hyperactivity, restlessness, poor memory, confusion, poor comprehension, poor concentration, poor physical coordination, difficulty in making decisions, stuttering or stammering, slurred speech, learning disabilities, poor physical coordination or clumsiness, numbness or tingling in hands or feet, mood swings, anxiety, fear or nervousness, anger, irritability or to aggressiveness, sadness or depression, frequent illness such as colds, frequent or urgent urination, genital itch or discharge, decreased libido and PMS. In another embodiment phenotypic data comprise data collected from one or more wearable devices.

Any suitable method of determining phenotype information from responses to the questionnaire(s), in particular information regarding an individual set of biological conditions for an individual, may be used. For example, a first biological condition may be assessed by examining the responses to a first subset of questions in the questionnaire(s); the questions in a subset may be weighted so that answers to some questions count more than others. Specific responses to individual questions in the first subset may be assigned specific numerical values, which can be adjusted according to the weight of the question, then the numerical values for all responses in the first subset are totaled to give a phenotype score for the first biological condition. A similar procedure may be followed to assess a second, different biological condition in the individual, using a second subset of questions in the questionnaire(s) to provide a phenotype score for the second biological condition; the second subset of questions may be the same as or different from the first subset. The process may be repeated for any suitable number of biological conditions; when biological conditions for an individual are determined from an overall set of biological conditions, the upper limit will, of course, be the number of biological conditions in the overall set (or fewer, if some of the biological conditions in the overall set are mutually exclusive). Thus, the process can be repeated for at least 2, 3, 4, 5, 6, 7, 8, 9, 10, 12, 15, 17, 20, 22, 25, 30, or 35 conditions, to produce the same number of phenotype scores; each different biological condition is assessed with reference to responses to its own specific subset of questions, which may be the same as or different from subsets for other biological conditions. Questions may belong to more than one subset for more than one biological condition, or may belong to only one subset.

Typically, determining the presence or absence of a condition and/or degree of the condition, also requires microbiome information for the individual, but in some cases phenotype information may be sufficient to determine presence or absence and/or degree of a biological condition in the individual. In these cases, to determine presence or absence of the condition, the phenotype score for the biological condition may be compared to a threshold value, and if the phenotype score is above the threshold value, or above or equal to the threshold value (or below the threshold value or below or equal to the threshold value, depending on the biological condition), then the biological condition is present, if not, it is not. Additionally, or alternatively, the biological condition may be assessed by assigning a degree to the condition, depending on the total phenotype score for the condition. Any suitable method of assigning degree may be used, such as quartiles, quintiles, percentage, and the like.

2. Omic Data

Methods and compositions herein can utilize one or more forms of "omic" data. "Omic" data generally refers to data about objects belonging to the same class. This includes, for example, data at the genomic, epigenomic, transcriptomic, proteomic, metabolomic, lipidomic, glycomic, immunomic, phenomic and exposomic levels. In certain embodiments "omic" data includes information about the microbiome of a subject. For example, the data could include genomic and/or transcriptomic microbiome data. It could also include "omic" data about a subject, such as, genomic or metabolomic data. Any suitable method of determining omic information for the individual may be used.

Microbiome can include gut, skin, mouth, nasal, vaginal and other microbial populations associated with an individual. In certain embodiments, information regarding the gut microbiome is used. A microbiome generally comprises heterogeneous microbial populations. Microbial communities are often made up of mixed populations of organisms, including unknown species in unknown abundances. Microbial components of the microbiome can include bacteria, archaebacteria, viruses, fungi, and protists. In some cases, information regarding one, two, three, four, or all of bacteria, archaebacteria, viruses, fungi, and protists can be used. In some cases, information regarding bacteria and viruses is used.

Microbiome information can be obtained in any suitable way, typically by analysis of one or more samples from the individual. Depending on the microbial populations of interest, any suitable sample or samples may be used. Exemplary samples include earwax, sweat, breast milk, hair, blood, bile, cerebrospinal fluid, lymphatic fluid, semen, vaginal discharge, menstrual fluid, feces (stool), sputum, urine, saliva, secretions from open wounds, secretions from the eye, skin tissue (e.g., a skin biopsy), subcutaneous tissue, muscle tissue, adipose tissue, and a combination thereof. Furthermore, a sample may be obtained from, for example, the gut, the vagina, the penis, a testicle, the cervix, the respiratory system, the ear, the skin, the rectum, the kidney, the liver, the spleen, the lung, the pancreas, the small intestine, the gallbladder, the lymph nodes, the colon, a nasal passage, the central nervous system, an oral cavity, a sinus, a nostril, the urogenital tract, an udder, an auditory canal, a breast, an open wound, the eye, fat, muscle, and combinations thereof. In certain embodiments, one or more stool samples from the individual is used to determine microbiome information for the individual.

Microbiome information useful in the methods and compositions discussed herein includes information regarding microbial taxa, such as genera, species and/or strains of the microbiome, e.g., gut microbiome as determined from one or more samples such as one or more fecal samples, such as species identities and/or quantities and/or relative quantities. Microbial information can also include expression information for various genes, indicating levels of transcription of various genes of the microbial species. Microbial information can also include biochemical information, such as information regarding small molecules produced by the microbial species of the microbiome.

The dataset can include data, or be derived from data, about nucleic acids present in a stool sample of a subject and/or from a blood sample of a subject. In either case, the data can be transcriptomic data. In the case of a stool sample, it can be data from microbial ribosomal RNA, which is useful for taxonomic information.

a) Information from Nucleic Acids

Polynucleotides can be extracted directly from the sample, or cells in the sample can first be lysed to release their polynucleotides. In one method, lysing cells comprises bead beating (e.g., with zirconium beads). In another method, ultrasonic lysis is used. Such a step may not be necessary for isolating cell-free nucleic acids.

Nucleic acids can be isolated from the sample by any means known in the art. Polynucleotides can be isolated from a sample by contacting the sample with a solid support comprising moieties that bind nucleic acids, e.g., a silica surface. For example, the solid support can be a column comprising silica or can comprise paramagnetic silica beads. After capturing nucleic acids in a sample, the beads can be immobilized with a magnet and impurities removed. In another method, nucleic acids can be isolated using cellulose or polyethylene glycol.

If the target polynucleotide is RNA, the sample can be exposed to an agent that degrades DNA, for example, a DNase. Commercially available DNase preparations include, for example, DNase I (Sigma-Aldrich), Turbo DNA-free (ThermoFisher) or RNase-Free DNase (Qiagen). Also, a Qiagen RNeasy kit can be used to purify RNA.

Alternatively, or in addition, a sample comprising DNA and RNA can be exposed to a low pH, for example, pH below pH 5, below pH 4 or below pH 3. At such pH, DNA is more subject to degradation than RNA.

If the target polynucleotide is RNA, the sample can be reverse transcribed into DNA. Reverse transcription generally takes place after a sample has been depleted of DNA.

In some aspects, a sample can be depleted of nucleic acids and nucleic acid species that are abundant relative to other nucleic acids in the sample. Some of the abundant nucleic acids may not be target nucleic acids (e.g., they may not encode sequence signatures or may not be informative of desired taxonomic information). The presence of these abundant nucleic acids can reduce the sensitivity of some of the methods described herein. This can be true, for example, if target or informative nucleic acids are rare relative to the abundant nucleic acids. Therefore, it can be advantageous to enrich a sample for target sequences by removing non-informative abundant sequences. Examples of sequences that can be removed include microbial ribosomal RNA, including 16S rRNA, 5S rRNA, and 23S rRNA. Other examples of sequences that can be removed include host RNA. Examples include host rRNA, such as 18S rRNA, 5S rRNA, and 28S rRNA.

Methods of enriching nucleic acid samples include the use of oligonucleotide probes. Such probes can be used for either positive selection or negative selection. Such methods often reduce the amount of non-target nucleotides.

If the target polynucleotide is DNA, then DNA can be isolated with silica, cellulose, or other types of surfaces, e.g., Ampure SPRI beads. Kits for such procedures are commercially available from, e.g., Promega (Madison, WI) or Qiagen (Venlo, Netherlands).

The isolated nucleic acids are generally sequenced for subsequent analysis. The methods described herein generally employ high throughput sequencing methods. As used herein, the term "high throughput sequencing" refers to the simultaneous or near simultaneous sequencing of thousands of nucleic acid molecules. High throughput sequencing is sometimes referred to as "next generation sequencing" or "massively parallel sequencing." Platforms for high throughput sequencing include, without limitation, massively parallel signature sequencing (MPSS), Polony sequencing, 454 pyrosequencing, Illumina (Solexa) sequencing, SOLID sequencing, Ion Torrent semiconductor sequencing, DNA nanoball sequencing, Heliscope single molecule sequencing, single molecule real time (SMRT) sequencing (PacBio), and nanopore DNA sequencing (e.g., Oxford Nanopore).

b) Transcriptome Sequence Preprocessing

Also provided herein are methods of analyzing RNA transcripts in a heterogeneous microbial sample. The RNA transcripts can be part of a transcriptome for a cell or cells in the heterogeneous microbial sample. Information regarding the transcriptomes of a plurality of cells from different species may be obtained. The methods generally include isolating and sequencing the RNA found in a sample as described above.

The sequences obtained from these methods can be preprocessed prior to analysis. If the methods include sequencing a transcriptome, the transcriptome can be preprocessed prior to analysis. In one method, sequence reads for which there is paired end sequence data are selected. Alternatively, or in addition, sequence reads that align to a reference genome of the host are removed from the collection. This produces a set of host-free transcriptome sequences. Alternatively, or in addition, sequence reads that encode non-target nucleotides can be removed prior to analysis. As described above, non-target nucleotides include those that are over-represented in a sample or non-informative of taxonomic information. Removing sequence reads that encode such non-target nucleotides can improve performance of the systems, methods, and databases described herein by limiting the sequence signature database to open reading frames can the size of the database, the amount of memory required to run the sequence signature generation analysis, the number of CPU cycles required to run the sequence signature generation analysis, the amount of storage required to store the database, the amount of time needed to compare sample sequences to the database, the number of alignments that must be performed to identify sequence signatures in a sample, the amount of memory required to run the sequence signature sample analysis, the number of CPU cycles required to run the sequence signature sample analysis, etc.

c) Metabolomic Data

The dataset also can include metabolomic data. For example, the dataset can include data about metabolic products in urine. Metabolites can be detected, for example, by gas chromatography/mass spectrometry or by NMR spectroscopy.

3. Taxonomic Data

Subject data can include taxonomic data about the taxonomic classification and amounts of microbes in a microbiome of the subject. Such data is typically derived from nucleic acid sequence data obtained from the subject's microbiome. 16S RNA sequences are a standard source of information for assigning taxonomic classifications. Non-rRNA transcriptome data as an alternative source of information for taxonomic classification. Such methods are described in international patent publication WO 2018/160899 ("Systems And Methods For Metagenomic Analysis"). Many metagenomic classifiers, aligners and profilers are publicly available. See, for example, Florian P Breitwieser et al., "A review of methods and databases for metagenomic classification and assembly," Briefings in Bioinformatics, Volume 20, Issue 4, July 2019, Pages 1125-1136, doi.org/10.1093/bib/bbx120, Published: 23 Sep. 2017. These include, without limitation, Centrfiuge, GOTTCHA, kraken, kraken2, CLARK, Kaiju, MetaPhlAn, MetaPhlAn2, MEGAN, LMAT, MetaFlow, mOTUs, and mOTUs2.

Taxonomic analysis can involve searching a sequence catalog of microbiome sequences for matches with sequences in the dataset, e.g., meta-transcriptomic sequences. Matches are assigned to the proper taxonomic category. Numbers of matches with a taxonomic category can indicate quantities of microbes of that taxonomic category in the sample.

The classifications can be at one or a plurality of different taxonomic levels, typically down to the species or strain level. Sequencing reads that map to sequences in the sub-catalog can then be labeled with tags indicating the taxonomic category at each level. The taxonomic label is assigned. Such systems can include classical or modern taxonomic classification systems.

As used herein, the term "taxon" (plural "taxa") is a group of one or more populations of an organism or organisms seen by taxonomists to form a unit. A taxon is usually known by a particular name and given a particular ranking. For example, species are often designated using binomial nomenclature comprising a combination of a generic name for the genus and a specific name for the species. Likewise, subspecies are often designated using trinomial nomenclature comprising a generic name, a specific name, and a subspecific name. The taxonomic name for an organism at the taxonomic rank of genus is the generic name, the taxonomic name for an organism at the taxonomic rank of species is the specific name, and the taxonomic name for an organism at the taxonomic rank of subspecies is the sub-specific name, when appropriate.

As used herein, the term "taxonomic level" refers to a level in a taxonomic hierarchy of organisms such as, strain, species, genus, family, order, class, phylum, and kingdom. In some embodiments, each taxonomic level includes a plurality of "taxonomic categories", that is, the different categories belonging to particular taxonomic level. Some taxonomic levels only include a single member.

As used herein, the term "species" is intended to encompass both morphological and molecular methods of categorization. Species can be defined by genetic similarity. In some embodiments, a cladistic species is an evolutionarily divergent lineage and is the smallest group of populations that can be distinguished by a unique set of morphological or genetic traits.

Genomes imported into the reference catalog are typically indexed with a genome number. Various taxonomy indices, such as the NCBI taxonomy, categorized each genome number into a taxonomic classification. Consequently, sequencing reads that match reference sequences can also be taxonomically classified based on the number. Accordingly, using a taxonomic tree implicit in the taxonomic designation taxonomic source of any sequencing read can be identified and classified.

Once classified, sequences in each category can be quantified or estimated to determine amounts of sequencing reads in each taxonomic category and the relative abundance of each taxonomic entity. The sequencing reads are meta-transcriptomic in origin. Accordingly, amounts of reads in a taxon represent transcriptional activity of the taxon, rather than pure numbers of organisms in the taxon in the sample.

4. Gene Expression Quantitation

The methods, systems and databases herein can be used to identify activity of a gene or a biochemical pathway present in the sample. In some embodiments, the methods include aligning sequencing reads to a database comprising open reading frame information that is associated with a particular biochemical activity or pathway, as described above. Some of such methods can include identifying taxonomic information for a sequence. Examples include the VIOMEGA algorithm (see WO 2018/160899 (Vuyisich et al.) or GOTT-CHA algorithm, which detects sequence signatures that identify nucleic acids as originating from organisms at various taxonomic levels. Nucleic Acids Res. 2015 May 26; 43(10): e69. Other methods include MetaPhlAn, Bowtie2, mOTUs, Kraken, and BLAST. Some of such methods do not include identifying taxonomic information for the sequence, but instead may identify the biochemical activity, pathway, protein, functional RNA, product, or metabolite associated with a particular sequence read or sequence signature.

"Gene expression," "gene activity" or "activity of a gene" is a generally a function of transcription, e.g., the quantity of RNA in a sample encoding the gene. This can be done at any taxonomic level. For example, gene expression could be a measure of activity of the gene in a single species, or it could be activity of the gene across organisms belonging to a common genus, class, order or phylum. The term "gene" can refer to orthologs of a gene across different species. Such orthologs can be identified, for example, with the KEGG orthology. Accordingly, the term "gene expression" also embraces gene function activity is understood by activity of functional orthologs.

5. Functional Activities and Functional Activity Scores

"Functional activities" are biological activity categories including biological or health functions or conditions at the cellular, organ or organismal level. Functional activities are assigned functional activity scores based on such data. Functional activity scores represent quantitative measures of functional activity. A functional category can involve any function related to health or wellness. Functional categories can embrace health parameters, health indicators, biological conditions and health risks. The activity of the function is assessed by analyzing -omic, e.g., transcriptomic data, which is collected from active, living organisms, e.g., expressing RNA from their genomes.

Functional activity includes integrative functional activities and non-integrative functional activities. Non-integrative functional activities are based on a single type of data or function, such as microbiome pathway activity data, taxa group activity data and host transcriptomic data. Integrative functional activities are based on an be based on a plurality of different kinds of data or functions. For example, such functional activities can combine pathway activity data in taxa activity data.

a) Score Elements (1) Pathways

In certain embodiments, functional activities include the activities of one or more pathways. As used herein, the term "pathways" refers to biological pathways, which are sequences of proven molecular events (such as enzymatic reactions or signal transduction or transport of substances or morphological structure changes) that lead to specific functional outcomes (such as secretion of substances, sporulation, biofilm formation, motility). Many biological pathways are known in the art, and examples can be found on the web at wikipathways.org/index.php/WikiPathways, pathwaycommons.org, and proteinlounge.com/Pathway/Pathways.aspx. Manual expert curation of scientific literature also can be used to reconstruct or create custom biological pathways. Biological pathways can include a number of genes that encode peptides or proteins, which play specific signaling, metabolic, structural or other biochemical roles in order to carry out various molecular pathways.

As used herein, the terms "biochemical activity" and "biochemical pathway activity" refer to activity of a biochemical pathway. Pathways of interest include, without limitation, butyrate production pathways, LPS biosynthesis pathways, methane gas production pathways, sulfide gas production pathways, flagellar assembly pathways, ammonia production pathways, putrescine production pathways, oxalate metabolism pathways, uric acid production pathways, salt stress pathways, biofilm chemotaxis in virulence pathways, TMA production pathways, primary bile acid pathways, secondary bile acid pathways, acetate pathways, propionate pathways, branched chain amino acid pathways, long chain fatty acid metabolism pathways, long chain carbohydrate metabolic pathways, cadaverine production pathways, tryptophan pathways, starch metabolism pathways, fucose metabolism pathways.

(2) Taxa Groups

In certain embodiments, functional activities include the activities of one or more taxa groups. Microbial taxa include taxonomic designation at any taxonomic level, e.g., species, genus, order or phylum. Active microbial taxa are taxa that are not really present but that are metabolically active, e.g., as measured by transcriptional levels of the microbial genome. Groups of microbial taxa whose activity contribute to functional activity in a functional category are referred to herein as "taxa groups". So, for example, pro-inflammatory taxa group can comprise one or more of: proteobacteria, opportunistic bacteria or pathogens, viruses; anti-inflammatory taxa group can comprise one or more of: butyrate producers, Lactobacilli and Bifidobacteria; intestinal barrier disruptors taxa comprise one or more of: *Ruminococcos torques, Ruminococcus gnavus, Serratia*, Sutterella, and other mucus-degrading or epithelial layer-disrupting organisms.

Taxa groups of interest include, without limitation, *Prevotella* (genus)/*Bacteroides* (genus) ratio, *Eubacterium rectale* (species), *Eubacterium eligens* (species), *Faecalibacterium prausnitzii* (species), *Akkermansia muciniphila* (species), metabolic-related probiotic species (functional group), *Roseburia* (genus), *Bifidobacterium* (genus), *Lactobacillus* (genus), *Clostridium butyricum* (species), *Allobaculum* (genus), Firmicutes (phylum)/Bacteroidetes (phylum) ratio, Lachnospiraceae (family), Enterobacteriaceae (family), *Ralstonia pickettii* (species), *Bilophila wadsworthia* (species).

b) Integrative Functional Activities

Examples of integrative functional categories include, without limitation, inflammatory activity, metabolic fitness, digestive efficiency, intestinal barrier health, protein fermentation, gas production, microbial richness, SIBO-like Pattern, detoxification potential (ability of microbiome to detoxify the body), gut neuro-balance (impact of microbiome on the brain, e.g., by production of neurotransmitters), neurological health, cardiovascular health, hormonal balance, musculoskeletal health, hepatic function, urogenital health, mitochondrial activity, immune function, gastrointestinal health, diabetes, skin conditions and infectious disease.

c) Hierarchical Functional Activities

Figure 4:
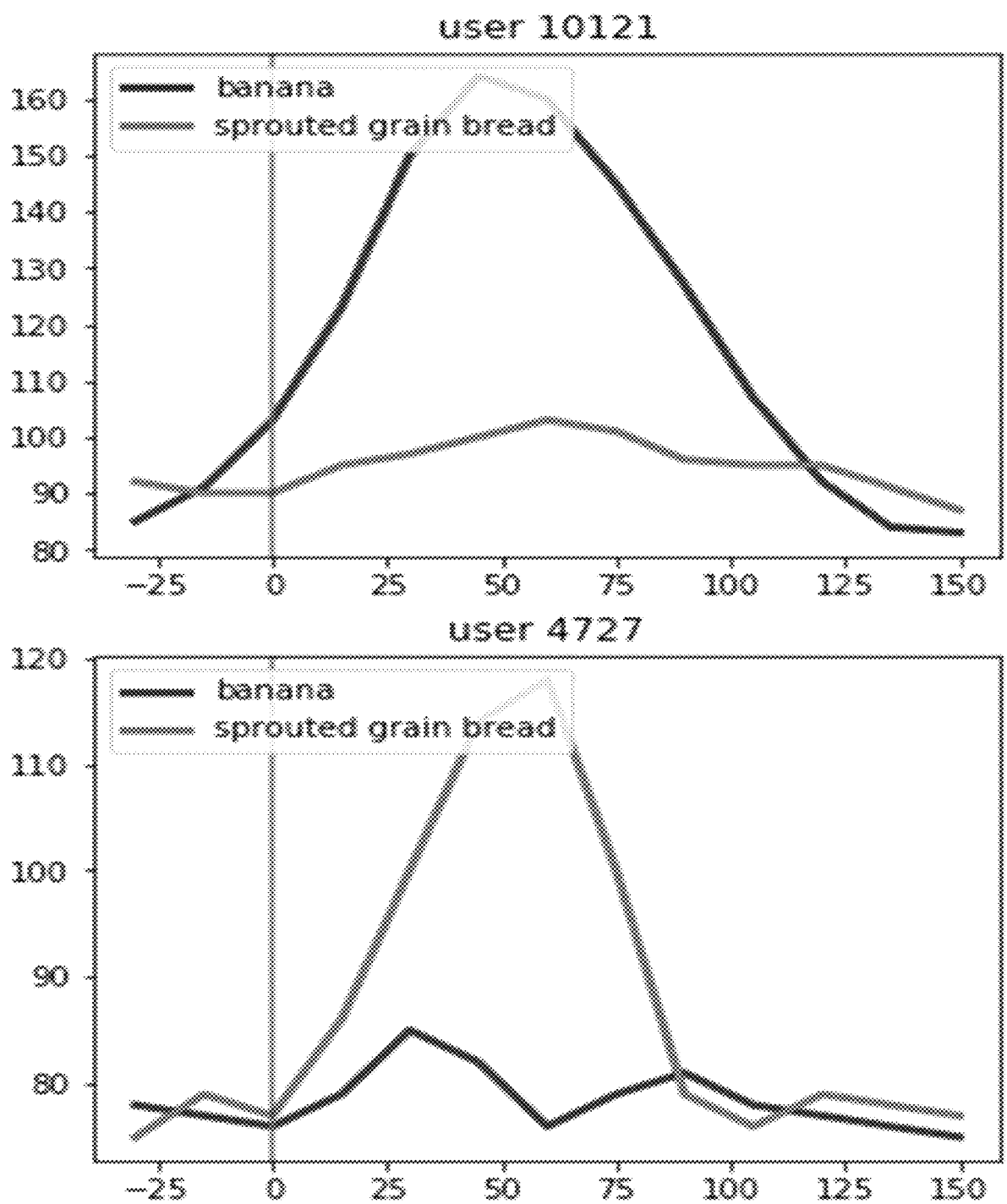
FIG. 4 shows glycemic response of two different individuals to two different foods (banana (light line) and sprouted grain bread (dark line).

Functional categories can be hierarchical in nature, with functional categories at lower levels in the hierarchy being aggregated into functional categories at higher levels in the hierarchy. For example, at a lowest level a single biochemical pathway or a group of microbial taxa can serve as a function category. Combinations of pathways and microbial taxa groups can be integrated into higher level categories. This includes, for example, a plurality of pathways, a plurality of taxa groups or at least one pathway and at least one taxa group. For example, inflammatory activity is a functional category that aggregated pro-inflammatory and anti-inflammatory components. Each of these components represents a functional category. In turn, each of the pro-inflammatory and anti-inflammatory categories aggregated scores from biochemical pathways and taxa groups. Referring to FIG. 4, a number of functional categories can be aggregated into a higher order functional category, in this case, digestive efficiency. More specifically, in this example, digestive efficiency aggregated scores from the categories protein fermentation, motility/gases, intestinal barrier health and SIBO-like/hypochlorhydrea pattern. While the final aggregated functional category is provided with a functional activity score, each sub functional category which is comprised within the highest functional category may itself be provided with a discrete score or other logic may be used to aggregate functional activities of the subcategories into the topmost functional category.

d) Functional Activity Score

A "functional activity score" refers to a measure assigned to an activity or state of a functional activity. A functional activity score can be assigned to a functional category in a subject based on -omic data, e.g., data from the microbiome, such as meta-transcriptomic data. A functional activity score can be determined, for example, based entirely on the score for a pathway functional activity. Alternatively, where the functional activity is a composite of more than one pathway and taxa activity scores, optimality can be determined by reference to scores in a population of individuals.

A functional activity score can be given as within or outside a reference value, such as a range. The reference value can be derived from values across a population of subjects. For example, the reference range may constitute a statistical range within the population, such as a standard deviation from the mean. Alternatively, the reference range may be determined by expert analysis, by logic and/or with reference to literature sources. The value can be given as a continuous or discrete variable. For example, discrete variables can be given as "low" "medium" or "high", with "medium" constituting the reference range. Both "low" and "high" may be outside the reference range. Alternatively, the score can be given as "good", "average" or "needs improvement". A score of "needs improvement" indicates a score outside of a reference range for which action is recommended.

A functional activity score outside of a reference range can be considered suboptimal and indicative of the presence of a functional activity condition.

Quantitative measures can be given as a discrete or continuous range. Quantitative measures can be absolute numbers or relative amounts, such as normalized amounts. Quantitative measures include statistical measures such as mean, variance and standard deviation. For example, a quantitative measure can be a number, a degree, a level or bucket. A number can be a number on a scale, for example 1-10. Alternatively, the quantitative measure can embrace a range. For example, ranges can be high, medium and low; severe, moderate and mild; or actionable and non-actionable. Buckets can comprise discrete numerals, such as 1-3, 4-6 and 7-10. quantitative measure (number, range, relative amount, etc.).

6. Biological Condition Data

Subject data also can include data about the state of one or more biological conditions of a subject. A biological condition can be a phenotypic condition that is either self-reported or inferred from questionnaire data, or a suboptimal functional activity score, e.g., a score outside a normal range. A high glycemic response also can be a suboptimal score. For example, a state of a condition can be, for example, a self-reported active or diagnosed biological condition, or a condition derived from a plurality of symptom questionnaire answers, or it can also be a suboptimal result of one or more of the functional pathway scores derived from omics data. For example, transcriptomic data can be analyzed to identify genes from which transcripts were transcribed and a quantitative measure of their transcription generates the values of gene expression. This information, in turn, can be analyzed to identify genes expressed relative to the reference CLIA cohort, which have known gene-encoded molecular functions (mapped to KEGG Orthology IDs). Multiple KOs are mapped to biochemical pathways and, based on each KO's relative transcription levels, as well as its curated importance in the context of each proprietary pathway score, yields a quantitative measure of the overall activity levels of multiple biological pathways of interest. For example, all pathways that culminate in microbial production of butyrate are assessed as part of the "Butyrate Production Pathways" score. Multiple scores can also be used for deriving a broader functional area score, which may include not only multiple pathway scores, but also microbial organisms and their activity levels. These are integrative functional scores, such as such as inflammatory activity, metabolic fitness, digestive efficiency, detoxification potential, and gut neurobalance, hormonal balance. Activity of biological functions can be derived from one or more input-omic data types and may include functional profiling of either microbial or human (host's) activity, such as energy production, mitochondrial health, stress response, and immune system, activation functions. Methods for determining states of biological conditions from "omic" data are described in, for example, International Patent Application WO 2019/209753, published Oct. 31, 2019 ("Systems And Methods For Inferring Scores For Health Metrics").

7. Meal Data

Also included in the dataset are data about foods/meals consumed by subjects. Such data can include information about nutritional value of a food/meal such as, macronutrient content and micronutrient content of a food/meal as well as total calories of the food/meal. Timing of when a food/meal is consumed also can be included. Nutritional information about a meal can be derived from information about individual foods included in a meal. For example, knowing that a meal included 4 ounces of salmon, 6 ounces of broccoli and 3 ounces of brown rice, one can determine the total calories of the meal, as well as total protein, total fat, total carbohydrate, total fiber and amounts of micronutrients included therein. Thus, such a dataset could include raw data on individual foods consumed and overall nutritional data can be calculated from this raw data.

Figure 2:
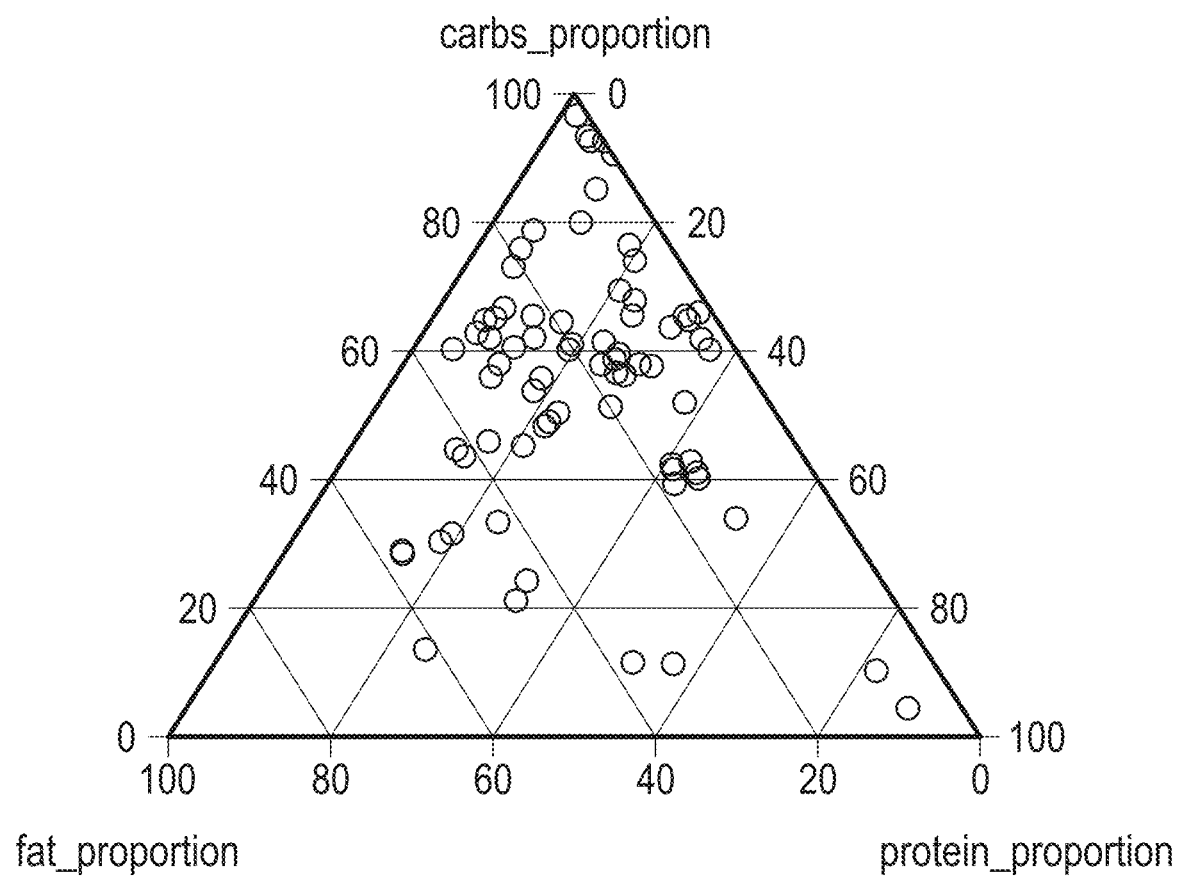
FIG. 2 shows exemplary macronutrient profiles of a plurality of meals.

Referring to FIG. 2, profiles shown include proportion of the meal by carbohydrate, fat and protein. Individual foods also can be mapped in the same manner such that predictions generated on nutritional content of meals can be translated into predictions based on nutritional content of individual foods.

8. Activity Data

The dataset can also include information about the activity of a subject. Such activity can include time, duration and quality of sleep. It also can include time, duration and intensity of exercise. Activity data can be collected, for example, through the use of wearable devices. Devices that record measurements of activity, such as steps, heart rate and sleep are commercially available. Sources include, for example, Apple, Samsung Fitbit, Garmin, Huawei, Amazfit, Nokia and Withings.

9. Glycemic Response Data

The dataset also includes information about the glycemic response of the subject after ingesting a meal. Glycemic response can be measured, for example, using a continuous glucose monitoring system. Such devices are commercially available from, for example Guardian, Dexcom and Medtronic.

Figure 3:
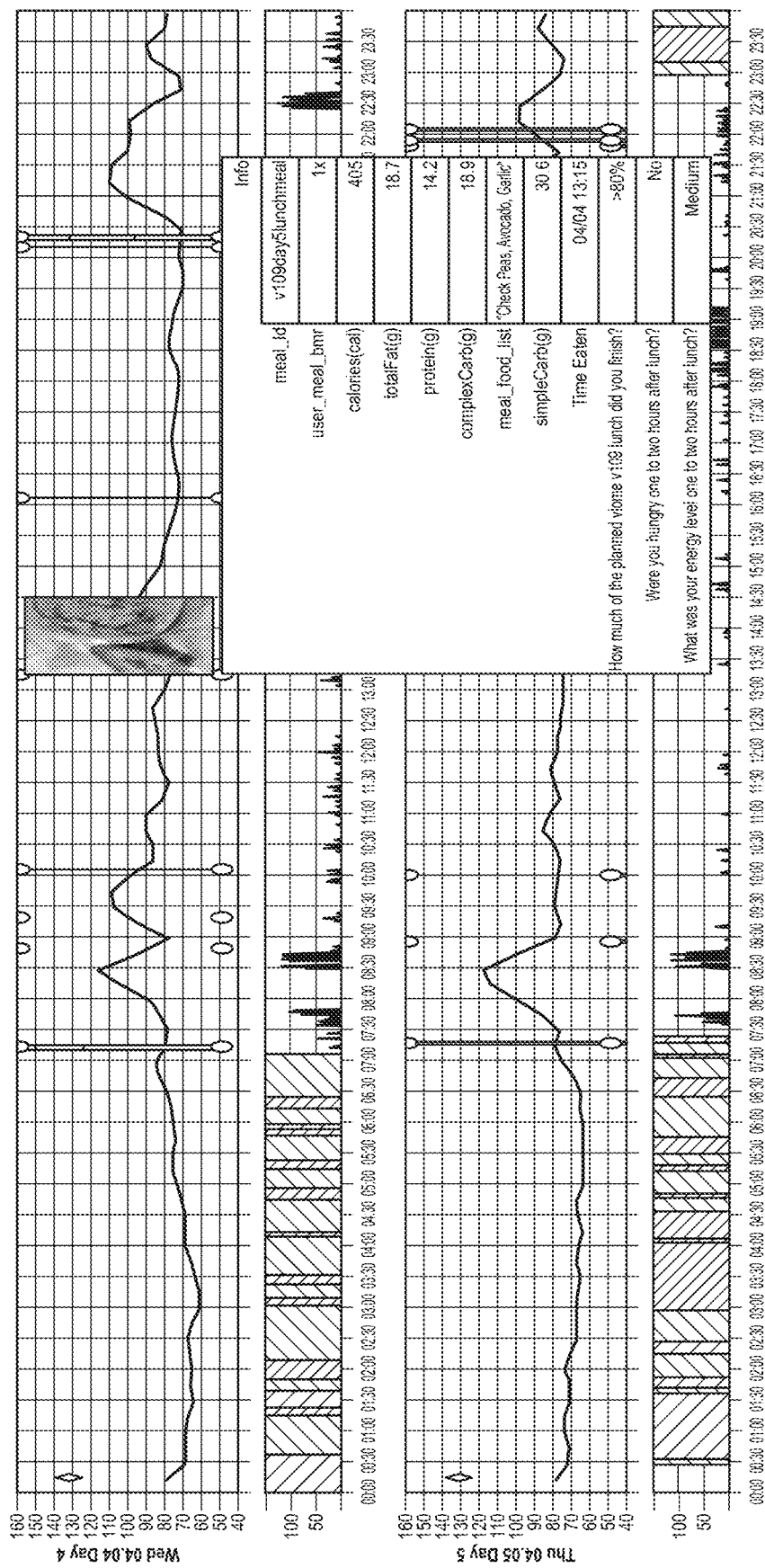
FIG. 3 shows an exemplary chart of a subject's blood glucose levels over the course of 24 hours.

Referring to FIG. 3, an exemplary chart shows a subject's blood glucose levels over the course of 24 hours. Vertical bars indicate consumption times of meals and snacks. Gray areas underneath each chart indicate times of sleeping and waking. Spikes indicate times of activity. Exemplary information for meal includes a meal ID, a user meal basal metabolic rate, Calories, total fat in grams, total protein in grams, complex carbohydrates in grams, a list of individual foods in the meal ("chickpeas, avocado, garlic"), simple carbohydrates in grams time eaten and subject responses to questions including: (1) Q. How much of the planned lunch did you finish? A. >80%; (2) Q. Were you hungry 1 to 2 hours after lunch? A. No; (3) What was your energy level 1 to 2 hours after lunch? A. Medium.

Referring to FIG. 4, glycemic response of two different individuals to two different foods (banana (light line) and sprouted grain bread (dark line)) can differ significantly. Results show that these two individuals had different responses to the same foods. More specifically, user 10121 showed a greater glycemic response to banana then to sprouted grain bread while user 4727 showed greater glycemic response to sprouted bread then to banana. This shows that an individual's glycemic response is not merely a function of the food's glycemic index.

Figure 5:
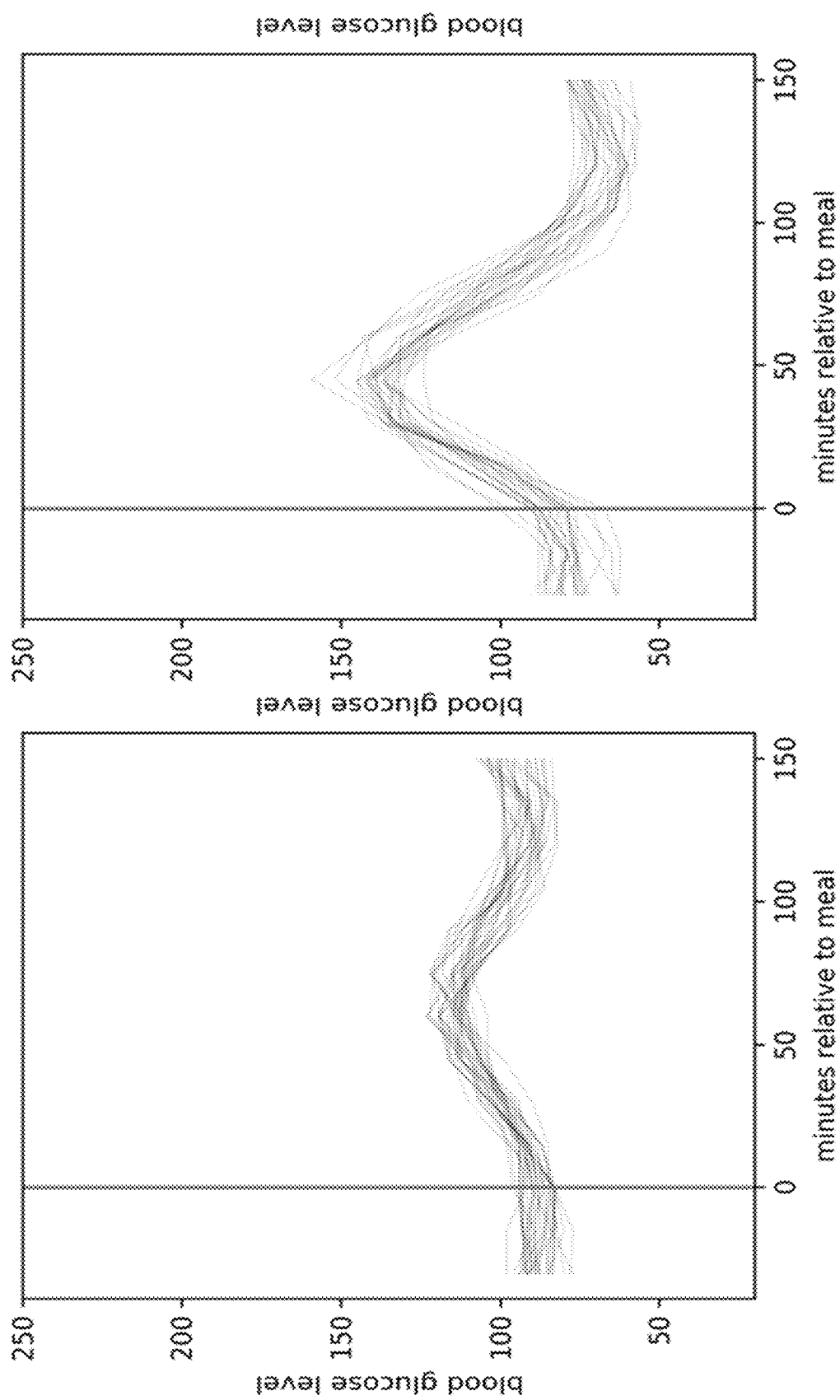
FIG. 5 shows groupings into clusters of similarly shaped glycemic response curves.

Raw data about glycemic response takes the form of blood glucose measurements over time. Typically, such time measurements begin about 30 minutes to one hour before a meal is consumed to about one hour, one- and one-half hours, two hours, 2½ hours or three hours after a meal is consumed. Referring to FIG. 5, curves of glycemic response can be grouped or classified into similar types. The vertical lines indicate time of the meal. The curves in panel A show a lower glycemic response than the curves of panel B. Meals/foods that produce the curves in panel A are labeled as "enjoy" foods. Meals/foods that produce the curves in panel B are labeled as "minimize" foods. Accordingly, glycemic response curves to more than 12,000 meals can be grouped into at least 50, at least 100, at least 200, at least 300, or at least 400 different curve shapes.

Glycemic response can be classified into a discrete or continuous range. Discrete ranges can include a plurality of discrete categories. These categories can be arranged hierarchically from least to greatest glycemic response. Categories can be provided as a binary choice, such as low and high. Such categories, in turn, can be labeled with quantitative or qualitative descriptors. For example, quantitative descriptors could include "low", "medium" or "high" glycemic response. Qualitative descriptors can be chosen to indicate a predicted health effect based on the glycemic response, or a desirability of consuming a food based on the predicted glycemic response. They can be related to the quantitative measure of glycemic response. So, for example glycemic response can be categorized into "more desirable" and "less desirable", or "acceptable" and "sub-optimal". Category descriptors can come with an implicit recommendation about food consumption such as, "superfood", "enjoy", "minimize" and "avoid".

Glycemic responses, e.g., based on curve shape classification, can be provided as a quantitative measure or relative descriptor of glycemic response. For example, glycemic response can be provided as a number on a continuous range from low to high.

Glycemic response may be measured as a function of area under the curve (AUC) of glucose measurements over time. Alternatively, classification of glycemic response can take into consideration the shape of the glycemic response curve. For example, curve factors can include, among other things, peak time, peak value, slope of the ascent, and descent.

B. Food Ontology

A food ontology is provided which contains information about macronutrient and micronutrient content of a plurality of different foods. The information can include a quantitative measure of the amount of a micronutrient or macronutrient in the food. For example, the quantitative measure can be an absolute amount, e.g., grams or micrograms, or a relative amount. For example, the food ontology can include a percent of weight or a percent of total calories of a macronutrient in the food. The number of different foods in the food ontology can be at least any of 100, 200, 300, 400, 500, 600, 700, 800, 900, 1000, 2500 and 5000. Exemplary foods that can be included in the food ontology include, for example, those listed in Table 1.

TABLE 1

| Exemplary Foods | | |
|---|---|---|
| Abalone | Artichoke | Beef (fatty, grass-fed) |
| Acacia Gum | Arugula | Beef (lean, grass-fed) |
| Adzuki Beans | Asparagus | |
| Agar Agar | Aspartame | |
| Agave Nectar | Avocado | Beer |
| Alfalfa Sprouts | Avocado Oil | Beet |
| Allspice | Bamboo Shoots | Beet Greens |
| Almond Milk (unsweetened) | Banana (small) | Beet Sugar |
| Almonds | Barley | Bell Pepper (organic) |
| Amaranth | Basil | |
| Anchovy | Bay Leaf | Black Beans |
| Apple (medium, organic) | Beans (baked or refried) | Blackberry |
| Apricot | Bean Sprouts | Black Eyed Peas |
| Black Tea (brewed) | Cassava | Black Pepper |
| Blueberry | Catfish | Coriander |
| Bok Choy | Cauliflower | Cornish Game Hen |
| | Caviar or Roe | Corn Syrup |
| | Cayenne Pepper | Corn Tortilla |

TABLE 1-continued

| Exemplary Foods | | |
|---|---|---|
| Bone Broth (fish) | Celeriac | (organic, non-GMO) |
| Bone Broth (mammal) | Celery (organic) | |
| | Celery Seed | Couscous |
| Bone Broth (poultry) | Chanterelle Mushrooms | Cranberry |
| Boston Beans | Chard | Crayfish |
| Boysenberry | Cheese | Cucumber |
| Brazil Nuts | Cherry (organic) | Cumin |
| Breadfruit | Chervil | Cured Meat |
| Broccoli | Chestnuts | Currant |
| Brown Mushrooms | Chia Seeds | Curry Powder |
| Brown Rice | Chicken (dark) | Daikon |
| Brown Sugar | Chicken (white) | Dandelion Greens |
| Brussels Sprouts | Chickpeas | Dates |
| Buckwheat | Chicory (root) | Dextrose |
| Buffalo | Chili Powder | Dill (fresh) |
| Bulgur | Chlorella | Duck |
| Burdock Root | Cilantro | Dungeness Crab, Pacific |
| Butter | Cinnamon | Eel |
| Cabbage | Cloves | Egg (large) |
| Cane Sugar | Cocoa (unsweetened) | Eggplant |
| Canned Vegetables | Coconut MCT Oil | Egg White |
| Canola Oil | Coconut Meat | Egg Yolk |
| Capers | Coconut Milk (unsweetened) | Elderberry |
| Caraway Seed | Coconut Oil | Emu |
| Cardamom | Coconut Water | Endive |
| Cardoon (thistle stem) | Cod, Alaskan | Enoki Mushrooms |
| Carob | Coffee (brewed, organic) | Escarole |
| Carrot | Collard Greens | Farro |
| Cashews | Haddock | Fava Beans |
| Fennel Bulb | Halibut, Pacific | Lima Beans |
| Fennel Seed | Hard Squash | Lime |
| Fenugreek Seed | Heavy Cream (33% fat) | Lobster |
| Fermented Vegetables | Hemp Hearts | Loganberries |
| Fiddlehead Ferns | Herbal Tea (brewed) | Lo Han |
| Fig | Herring | Lotus Seeds |
| Filberts | Hickory Nuts | Lychee |
| Filberts or Hazelnuts | Honey | Maca |
| Flax Oil | Horseradish | Macadamia Nuts |
| Flax Seeds | Hot Pepper (organic) | Mace |
| Flounder | Huckleberry | Mackerel |
| Freekeh | Hydrogenated Vegetable Oil | Maitake Mushrooms |
| French Fries | Iodized Salt | Maltose |
| Fruit Juices | Jackfruit | Mango |
| Game Meat (venison, elk) | Jerusalem Artichoke | Mangosteen |
| Garlic | Jicama | Manuka Honey |
| Ghee | Kale | Maple Syrup |
| Ginger | Kamut | Margarine |
| Goat | Kasha | Marionberry |
| Goat Cheese | Kefir | Marjoram |
| Goat Milk | Kimchi | Melon |
| Goji Berry | Kiwi | Millet |
| Goose | Kohlrabi | Miso |
| Gooseberry | Kombucha | Molasses |
| Gourd | Kumquat | Morel Mushrooms |
| Granola Bars | Lamb | Mulberries |
| Grapefruit | Lard | Mushrooms |
| Grape Leaves | Leek | Mussel |
| Grape Seed Oil | Lemon | Mustard Greens |
| Grapes (organic) | Lentils | Mustard Seed |
| Green Beans | Lettuce | Natto |
| Green Tea (brewed) | Poppy Seed | Nectarine (organic) |
| Guava | Pork (lean) | Nutmeg |
| Oatmeal (flavored) | Portabella Mushrooms | Saffron |
| Oats | Potato (small, organic) | Sage |
| Octopus | Processed Cheese | Salmonberry |
| Okra | Processed Meat | Salmon, Pacific (wild-caught) |
| Olive Oil | | Sardine |
| Olives | | Sauerkraut |
| Onion | | Savoury |
| | | Scallops |
| | | Scrod |

TABLE 1-continued

Exemplary Foods

| | | |
|---|---|---|
| Orange | Prunes | Sea Salt or |
| Oregano | Pummelo | Himalayan Salt |
| Ostrich | Pumpkin | Seaweed (fresh) |
| Oyster | Pumpkin Seeds | Sesame Seeds |
| Mushrooms | Quail | Sheep Cheese |
| Papaya | Quinoa | Sheep Milk |
| Paprika | Radicchio | Shellfish Clam |
| Parsley | Radish | Shellfish Oyster |
| Parsnip | Rainbow Trout | Shitake |
| Passionfruit | Raisins | Mushrooms |
| Peach | Raspberry | Shortening |
| Peanuts | Red Beans | Shrimp |
| Pear (organic) | Red/Green/ | (domestic) |
| Peas | Romaine Lettuce | Snap Peas |
| Pecans | Rhubarb | Soda (regular or |
| Peppermint | Rice Cakes | diet) |
| (fresh) | (flavored) | Sole |
| Perch | Rice Milk | Sour Cherries |
| Persimmon | Rice Noodles | Sour Cream |
| Pheasant | Ricotta or | Soybeans (non- |
| Pickle | Cottage Cheese | GMO) |
| (unsweetened) | (2% fat) | Soy Milk |
| Pineapple | Rosemary (fresh) | (unsweetened) |
| Pine Nuts | Rutabaga | Spearmint (fresh) |
| Pinto Beans | Rye (sprouted | Spinach (organic) |
| Pistachios | bread) | Spirulina |
| Plantain | Saccharin | |
| Plum | Safflower Oil | |
| Pomegranate | Walnuts | |
| Sprouted Radish | Water Chestnuts | |
| Seeds | Watercress | |
| Squid | Wheatgrass | |
| Star Fruit | Wheat (sprouted | |
| Stevie | bread) | |
| Strawberry | Whey | |
| (organic) | White Beans | |
| Straw | White Flour | |
| Mushrooms | White Rice | |
| Sucrelose | White Tea | |
| Sugar (white) | (brewed) | |
| Summer Squash | Whole Milk | |
| Sunflower Seeds | Wild Rice | |
| Sweet Potato/ | Wine | |
| Yam | Xanthan Gum | |
| Swiss Chard | Xylitol | |
| Tapioca | Yam or Sweet | |
| Taro | Potato | |
| Tarragon | Yeast | |
| Tempeh | Yogurt (flavored) | |
| Thyme | Yogurt (plain) | |
| Tilapia | Zucchini Squash | |
| Tofu | | |
| Tomato (organic) | | |
| Triticale | | |
| Tuna (pole | | |
| caught) | | |
| Turbot | | |
| Turkey (dark) | | |
| Turkey (white) | | |
| Turmeric | | |
| Turnip | | |
| Vanilla Extract | | |
| Veal | | |
| Vinegar | | |
| Vinegar Apple | | |
| Cider | | |

Macronutrient information about each food in the food ontology can include, for example, one, two, three or four macronutrients selected from carbohydrates, fiber (generally indigestible carbohydrates), proteins, and fats.

Micronutrient information about each food in the food ontology can include any of vitamins (e.g., water-soluble vitamins and fat-soluble vitamins) and minerals (e.g., macro minerals and trace minerals). Water-soluble vitamins include, for example, Vitamin B1 (thiamine), Vitamin B2 (riboflavin), Vitamin B3 (niacin), Vitamin B5 (pantothenic acid), Vitamin B6 (pyridoxine), Vitamin B7 (biotin), Vitamin B9 (folate), Vitamin B12 (cobalamin), and Vitamin C (ascorbic acid). Fat-soluble vitamins include, for example, vitamin A, vitamin D, vitamin E and vitamin K. Macro minerals include, for example, calcium, phosphorus, magnesium, sodium, chloride, potassium and sulfur. Trace minerals include, for example, iron, manganese, copper, zinc, iodine, fluoride and selenium.

The food ontology also can include quantitative measures of one or a plurality of specific compounds listed in Table 2.

TABLE 2

Exemplary Specific Compounds

| | | |
|---|---|---|
| Adenine Nutrient | Aglycone | Absorbable |
| Allicin | Alliin | Carbohydrate |
| Alpha Linolenic Acid | amino acids | Allergen Protein |
| Anthocyanidin Nutrient | Anthocyanin | Allyl Cysteine |
| Arginine | Ascorbic Acid | Anethole |
| Avenanthramide | Avenanthramide | Apigenin |
| Nutrient | Phenolic Acid | Avenanthramide |
| B vitamins | Beta Carotene | B carotene |
| Biotin | Butyrate | Beta Glucan Cereal |
| Caffeine | Caffeine Nutrient | Butyric Acid |
| Calcium Ion2 | Capsaicin | Calcium |
| Casein2 | Catechin | Casein1 |
| Choline | Citrulline | Cholesterol |
| CoEnzymeQ10 | Collagen | Cobalamin |
| Cyanidin | Daidzein | Delta-7-sterine |
| Cysteine | Dodecanoic Acid | EGCG |
| Deta-sitosterol | (Lauric Acid) | Ellagic Acid |
| EicosaPentanoicOmega3 | ELLAGIC | Essential fatty acids |
| Epicatechin | Epigallocatechin | ferulic acid |
| Fatty Acid | Gallate | folate |
| Nutrient_Omega3 | Fatty Acid | FructOligoSaccharide |
| fiber | Nutrient_Omega9 | GamaAmino |
| folic acid | Flavonoid Nutrient | ButyricAcid |
| Fructose | FOS | gingerol |
| GammaAmino | GalactOligoSaccharide | Glucobrassicin |
| ButyricAcid | GammaLinolenicAcid | glucosinolates |
| Gingerol Nutrient | GLA | GlycemicIndex |
| Glucoraphanin | GlucosinolateNutrient | glycoside |
| Glutamine | GLUTEN | Inulin |
| Guanine Nutrient | GlycemicIndex/ | iridoid glycoside |
| iodine | Glycemic Load | kampferol |
| iron | Hypoxanthine | Lactose |
| Lactalbumin Alpha | Nutrient | Lignan Nutrient |
| lauric acid | Iodine Nutrient | Linoleic Acid |
| Limonin Glucoside | IronIon2 | Luteolin |
| Lutein | Lactalbumin Beta | Magnesium Ion2 |
| Lycopene | Lectin | medium chain |
| Maltose | Linalool | MUCIN |
| triglycerides | Lutein Zeaxanthin | niacin |
| Medium Chain | magnesium | Oleic Acid |
| Fatty Acid | Mannitol | phospholipids |
| Nutrient | Mucilage | phytonutrients |
| MUFAs | Naringenin | Polyphenol Nutrient |
| Nitrate | Nitrite | Polysaccharide |
| OXALATE | pantothenic acid | Insoluble |
| phosphorus | Phytonutrient Nutrient | Nutrient |
| Phytosterol Nutrient | phytosterols | potassium |
| polyphenols | Polysaccharide | probiotics |
| Polysaccharide Soluble | Insoluble | Quercetin |
| Fiber Nutrient | Fiber Nutrient | Retinoid Nutrient |
| Potassium Ion | Polysaccharide | Saponin Glycoside |
| protein | Soluble | Saturated |
| Resistant Starch | Nutrient | Triacylglycerol |
| Nutrient | Potassium Ion1 | Fat |
| riboflavin | pyridoxine | Sesquiterpene Lactone |
| Saponin Phytonutrient | resveratrol | SodiumIon1 |
| selenium | S Adenosyl | Theanine |
| Sinigrin | Methionine | thiamin |
| Sorbitol | saponins | Total Anthocyanidin |
| Theobromine Nutrient | Selenium Nutrient | Total Fiber |
| thiamine | sodium | Carbohydrate |
| Total Carbohydrate By | Tannoid Nutrient | Total Goitrogen |
| Difference Nutrient | Theophylline Nutrient | Total Oxalate |

TABLE 2-continued

Exemplary Specific Compounds

| | | |
|---|---|---|
| Total FructoOligosaccharide | thiols | Total Protein |
| Total Inulin | Total Copper | Tryptophan |
| Total Phosphorous | Nutrient | Vitamin E |
| Total Purine | Total GalactoOligo- | Vitamin B6 |
| VitAIU | saccharide | Vitamin E |
| Vitamin A | Total Iron | VITB2_Total Riboflavin |
| Vitamin C | Total Polyphenol | VITB6_Total PLP |
| Vitamin K | Total Sulfur | VITE |
| VITB3_Total Niacin | Vitamin C | Zeaxanthin |
| VITB9 | Vitamin B12 | |
| VITK_TotalMK | Vitamin D | |
| Zinc | VIT B | |
| | VITB5_Total Pantothenic Acid | |
| | VITB9_Total Folate | |
| | Xanthine Nutrient | |
| | Zinc Ion2 | |

III. Building Models Predicting Glycemic Response

Models can be created by statistical methods, including, for example, methods performed by machine learning. Machine learning involves training machine learning algorithms on training data sets comprising data from a plurality of test subjects.

Methods for generating models to predict glycemic response can comprise the following operations. A dataset as described above is provided. The dataset includes, for each of a plurality of subjects, phenotypic data, omic data, meal data and glycemic response data. Optionally, the dataset can further include activity/sleet data. Omic data can comprise gut microbiome data and/or blood transcript on data and/or urine metabolism data. Omic data may, in turn, be abstracted into microbial taxa data (e.g., types and amounts of microbes) and/or functional data. The -omic data used can be at any level of abstraction. So, for example, the -omic data used can include raw transcriptomic data, for example, sequence data subject to preprocessing. It also can include taxonomic data, that is, measures of various taxonomic categories derived from sequence data. It also can include gene expression data, which itself can be derived from sequence data and can be directed at the specific gene level or at the functional level, e.g., at the level of KEGG orthology. At a still higher level, the data input can include functional activity scores, at any hierarchical level. Accordingly, the features used to make inferences can be biochemical pathway activity scores, taxa group scores, or integrative functional activity scores. The data set is used as a training dataset to train a machine learning to algorithm to produce one or more models that predict glycemic response of a subject to a meal profile based on the phenotypic data and the omic data. Because each food in the food ontology has a nutritional profile that can be matched to a meal profile present in the meal data model can predict glycemic response based on food's nutritional profile.

1. Machine Learning Algorithms

The machine learning algorithm can be any suitable supervised machine learning algorithm, parametric or non-parametric. Machine learning algorithms include, without limitation, artificial neural networks (e.g., back propagation networks), decision trees (e.g., recursive partitioning processes, CART), random forests, discriminant analyses (e.g., Bayesian classifier or Fischer analysis), linear classifiers (e.g., multiple linear regression (MLR), partial least squares (PLS) regression, principal components regression (PCR)), mixed or random-effects models, non-parametric classifiers (e.g., k-nearest neighbors), support vector machines, and ensemble methods (e.g., bagging, boosting).

IV. Classifying Glycemic Response of a Food Subject to a Food

Using a classifier as described above, and operator can classify the glycemic response of one or a plurality of foods in the food ontology for a particular subject based on phenotypic data and omic data from the subject. The number of foods classified can be, for example, at least one, at least two, at least 10, at least 50, at least 100, at least 250, at least 500 or at least 1000 different foods. The classifier can classify the food according to any classification scheme useful to the operator. This can include, for example, a binary classification, such as (low) and (high) or, according to a numeric scale, such as a 1-10 scale. Glycemic response can be classified as "high" or "low", with "high" representing a stronger response.

Food classifications, e.g., "high" or "low" can be provided to a subject for example, in the form of recommendations. In one embodiment, the recommendations include a positive recommendation to consume (e.g., "enjoy") for foods inferred to produce a lower glycemic response in the subject, and a negative recommendation to consume (e.g., "minimize") for foods inferred to produce a higher glycemic response in the subject.

V. Food Recommendations Incorporating Personalized Glycemic Responses

Inferences about glycemic response can be incorporated into methods that further personalize recommendations for foods in a food ontology. Such methods further incorporate information about food micronutrients, phenotype conditions (e.g. health conditions) and microbiome analysis. The incorporation of this information can allow classification of foods into more or finer categories then provided with glycemic response predictions alone. Certain of these methods are further described in International Patent application PCT/US 2019/055270, filed, Oct. 8, 2019 (Banavar et al., "Methods for and Compositions for Determining Food Item Recommendations").

Figure 7:
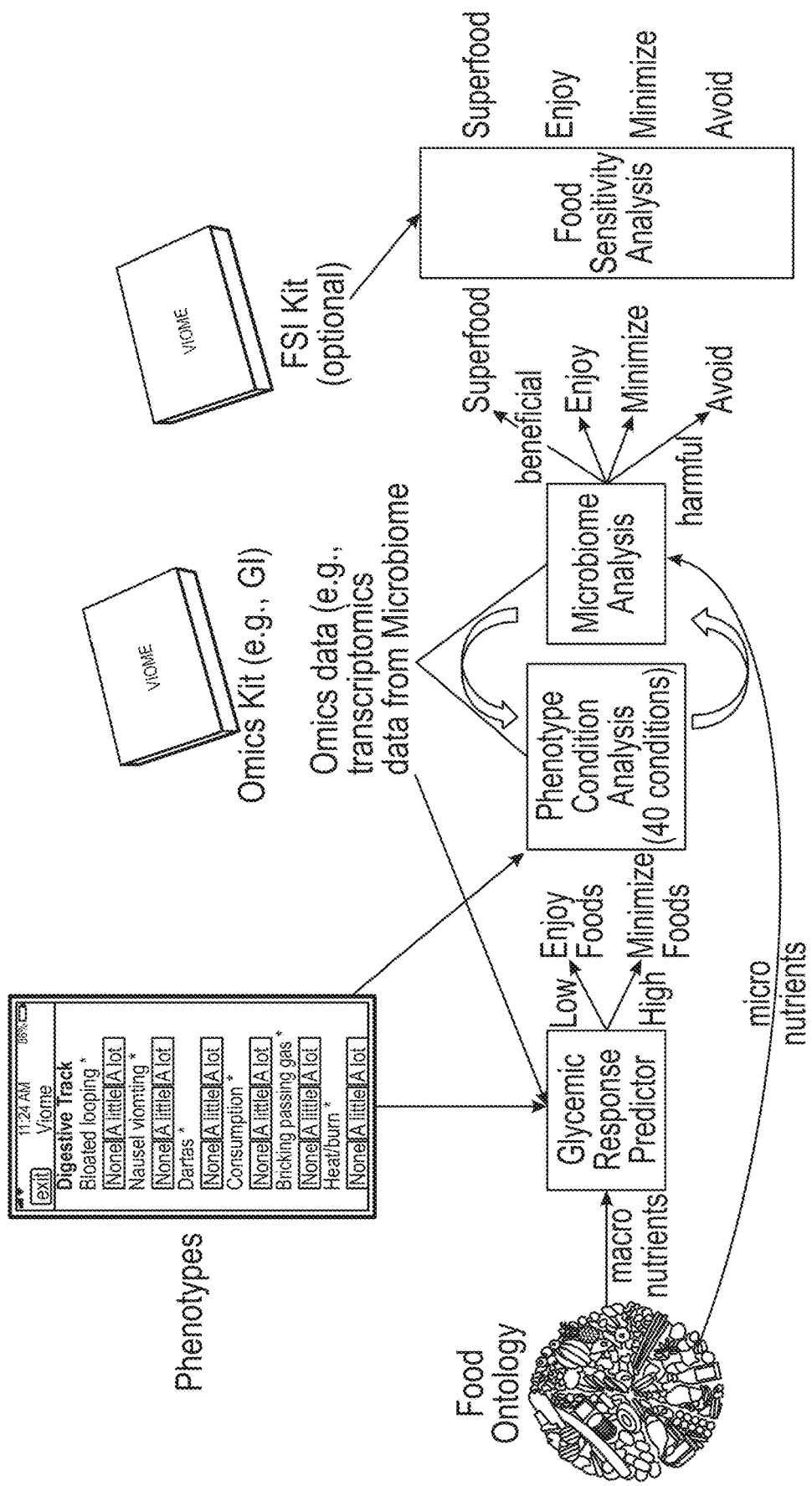
FIG. 7 shows an exemplary recommendation engine pipeline architecture.

Referring to FIG. 7, an exemplary recommendation engine pipeline can have an architecture as follows. The architecture includes a food ontology that includes macronutrient and micronutrient information about each of a plurality of foods. The food ontology is developed from food chemistry information culled from authoritative sources. A glycemic response predictor that predicts glycemic response of an individual to a food takes into consideration information about the phenotype of the subject, omic information from the subject including, for example, microbiome transcriptome information and macronutrient information about the food from the food ontology. The glycemic response predictor classifies a food as "low" or "high", which can be translated as "enjoy foods" and "minimize foods", respectively. Food so classified can be further categorized as more beneficial ("superfood") or more harmful ("avoid").

Reclassification can involve use of a reasoning module developed from knowledge (facts & rules) elicited from clinical and biology experts. This module can use predicted or confirmed phenotype conditions (e.g., health conditions) of a subject as well as omic information from the subject, such as analysis of the effect of micronutrients in the food on the subject's microbiome. Together, this information is used to predict whether the food is likely to improve or worsen one or more phenotype conditions. Foods classified as producing a relatively low glycemic response or a relatively high glycemic response may be further found to produce beneficial effects or harmful effects on the subject's biological conditions. Accordingly, a food classified as "enjoy" that is determined to have a beneficial effect can be upgraded to a "superfood" category. A food classified as "enjoy" that is determined to have a harmful effect can be downgraded to a "minimize" category. A food classified as "minimize" that is determined to have a beneficial effect can be upgraded to a "enjoy" category. A food classified as "minimize" that is determined to have a harmful effect can be downgraded to a "avoid" category. Foods can be further upgraded or downgraded based on a subject's sensitivity to the food.

In certain embodiments one or a plurality of phenotype conditions for a subject is identified. Such conditions can be the result of medical analysis, or, can be inferred from phenotype data and omic data from a subject. Such conditions can include, for example, a condition from Table 3.

TABLE 3

Exemplary Biological Conditions

| | | |
|---|---|---|
| Abdominal Weight | Diverticular Condition | Insomnia |
| Acne | Dysbiosis | Leaky Gut Condition |
| Attention Deficit Disorder | DysGlycemia | Liver Condition |
| Allergy | (hyperglycemia) | Lung Condition |
| Allergy ENT Condition | Dysmotility | Male Hormone |
| Allergy Lung Condition | ENT Condition | Condition |
| Allergy Skin Condition | Eye Condition | Muscle Condition |
| Anxiety | Female Hormone | Nerve Condition |
| AutoImmune | Condition | Nutritional |
| Autoimmune Gut | Food Reaction | Deficiency |
| Condition | GERD | Obese |
| Autoimmune Joint | GI Inflammation | Overweight |
| Condition | Headache Condition | Small Intestinal |
| Autoimmune Skin | HypoGlycemia | Bacterial |
| Condition | HypoThyroid Condition | Overgrowth |
| Cardiovascular Condition | Infection Condition | Thyroid Condition |
| Depression | | |

The impact of a food on a condition of a subject can be determined based on the glycemic response classification of the food (e.g., determined as described herein), the impact of micronutrients in the food's micronutrient profile on the microbiome of the subject and the relative impacts of the micro biome or changes in it to the biological condition and vice versa. In certain cases, the relative impact of a food on the subject's microbiome and impact of the glycemic response on the condition will be weighed against each other in determining whether to modify the classification of a food on the subject. For example, an individual may have a plurality of biological conditions which are differently affected by the food. Also, the impact of a food on the microbiome of the subject may have a disproportionate effect on the biological condition compared with the expected glycemic response of food based on micronutrient content.

Recommendations also can include recommendations for a subject to take one or more supplements expected to improve the state of biological condition the subject. Exemplary supplements for consumption include those in Table 4.

TABLE 4

Exemplary Supplements

| Supplement | Category |
|---|---|
| ABx Support | Probiotics |
| Atrantil | Digestive Support |
| Berberine | Polyphenols |
| BioPro | Probiotics |
| Cal-Mag Butyrate | Gut Support |
| Digestive Enzymes Ultra with Betaine HCl | Digestive Enzyme |
| Formula 20 | Digestive Enzyme |
| Gastrus | Probiotics |
| GI Revive | Digestive Support |
| Glutathione-SR | Antioxidant |
| Iberogast | Prokinetic |
| Klean Probiotic | Probiotics |
| Lactoprime Plus | Probiotics |
| Meriva 500-SF | Polyphenols |
| Ortho Biotic | Probiotics |
| PaleoFiber | Prebiotic |
| Panplex 2 Phase | Digestive Enzyme |
| PhytoGanix | Polyphenols |
| Polyresveratrol SR | Polyphenols |
| Pomegranate Plus | Polyphenols |
| Prebiotic Powder | Prebiotic |
| Pro 15 | Probiotics |
| Resveratrol Supreme | Polyphenols |
| Spectra Reds | Polyphenols |
| Theracurmin HP | Polyphenols |
| Theraflavone | Polyphenols |
| Therbiotic Complete | Probiotics |
| Therbiotic Factor 6 | Probiotics |
| Ultraflora Spectrum | Probiotics |
| Vital 10 | Probiotics |
| VSL 3 Pouch | Probiotics |

VI. Systems

Also provided herein are systems comprising a computer. Such systems can be used for, among other things, executing learning algorithms, executing classification algorithms to predict glycemic response. Computer systems can include a central processing unit (also referred to as a CPU or a processor) memory (e.g., random-access memory, read-only memory, flash memory), communication interface for communicating with one or more other systems, and peripheral devices.

Such systems can be connected through a communications network to the Internet. The communications network can be any available network that connects to the Internet. The communication network can utilize, for example, a high-speed transmission network including, without limitation, Digital Subscriber Line (DSL), Cable Modem, Fiber, Wireless, Satellite and, Broadband over Powerlines (BPL).

Figure 8:
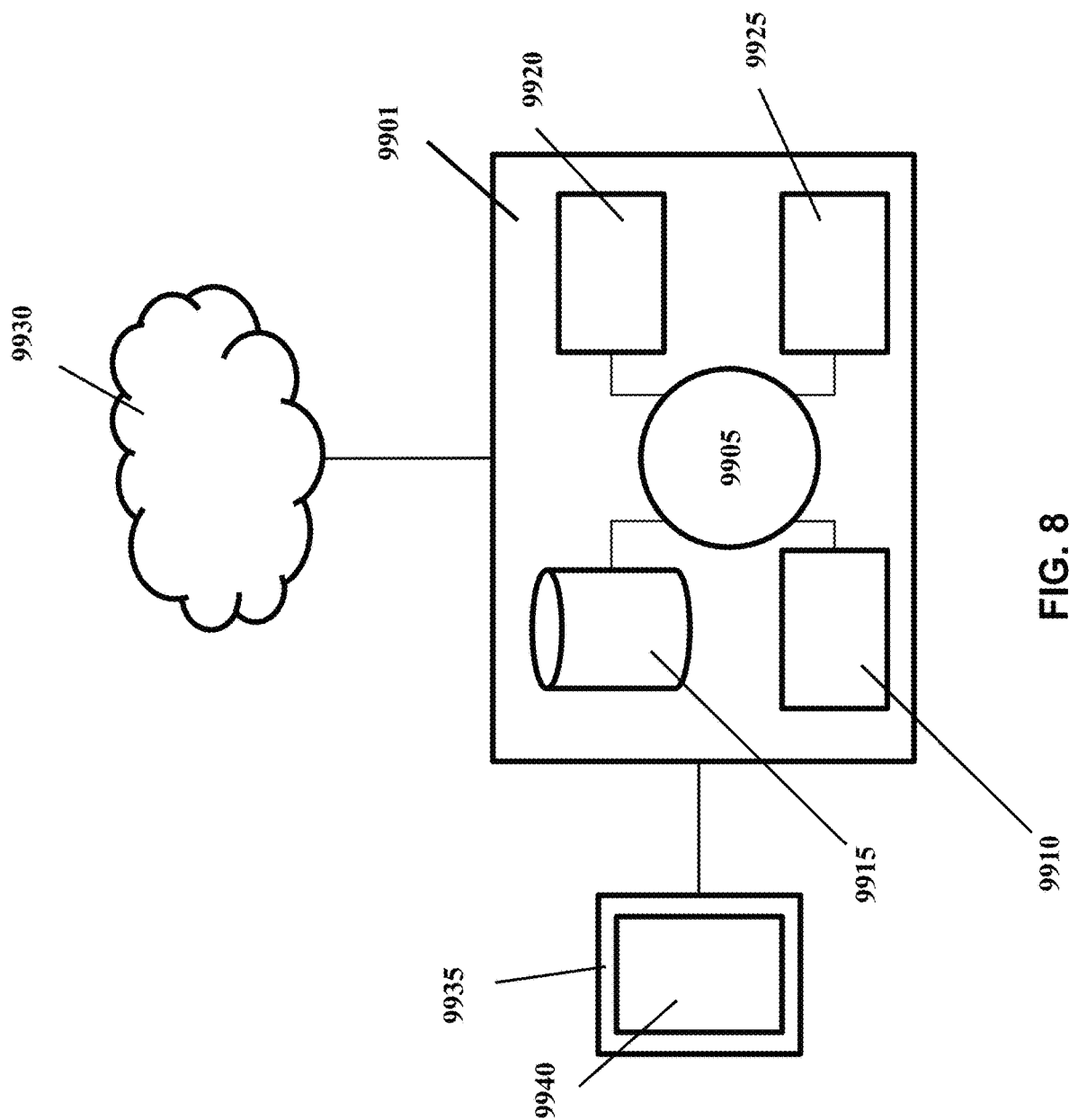
FIG. 8 shows an exemplary computer system.

FIG. 8 shows an exemplary computer system. The computer system 9901 includes a central processing unit (CPU, also "processor" and "computer processor" herein) 9905, which can be a single core or multi core processor, or a plurality of processors for parallel processing. The computer system 9901 also includes memory or memory location 9910 (e.g., random-access memory, read-only memory, flash memory), electronic storage unit 9915 (e.g., hard disk), communication interface 9920 (e.g., network adapter) for communicating with one or more other systems, and peripheral devices 9925, such as cache, other memory, data storage and/or electronic display adapters. The memory 9910, storage unit 9915, interface 9920 and peripheral devices 9925 are in communication with the CPU 9905 through a communication bus (solid lines), such as a motherboard. The storage unit 9915 can be a data storage unit (or data repository) for storing data. The computer system 9901 can be operatively coupled to a computer network ("network") 9930 with the aid of the communication interface 9920. The network 9930 can be the Internet, an internet and/or extranet, or an intranet and/or extranet that is in communication with the Internet. The network 9930 in some cases is a telecommunication and/or data network. The network 9930 can include one or more computer servers, which can enable distributed computing, such as cloud computing.

The CPU 9905 can execute a sequence of machine-readable instructions, which can be embodied in a program or software. The instructions may be stored in a memory location, such as the memory 9910. The instructions can be directed to the CPU 9905, which can subsequently program or otherwise configure the CPU 9905 to implement methods of the present disclosure.

The storage unit 9915 can store files, such as drivers, libraries and saved programs. The storage unit 9915 can store user data, e.g., user preferences and user programs. The computer system 9901 in some cases can include one or more additional data storage units that are external to the computer system 9901, such as located on a remote server that is in communication with the computer system 9901 through an intranet or the Internet.

The computer system 9901 can communicate with one or more remote computer systems through the network 9930.

Methods as described herein can be implemented by way of machine (e.g., computer processor) executable code stored on an electronic storage location of the computer system 9901, such as, for example, on the memory 9910 or electronic storage unit 9915. The machine executable or machine-readable code can be provided in the form of software. During use, the code can be executed by the processor 9905. In some cases, the code can be retrieved from the storage unit 9915 and stored on the memory 9910 for ready access by the processor 9905. In some situations, the electronic storage unit 9915 can be precluded, and machine-executable instructions are stored on memory 9910.

Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks.

The computer system 9901 can include or be in communication with an electronic display 9935 that comprises a user interface (UI) 9940 for providing, for example, input parameters for methods described herein. Examples of UIs include, without limitation, a graphical user interface (GUI) and web-based user interface.

Processes described here can be performed using one or more computer systems that can be networked together. Calculations can be performed in a cloud computing system in which data on the host computer is communicated through the communications network to a cloud computer that performs computations and that communicate results to a user through a communications network. For example, nucleic acid sequencing can be performed on sequencing machines located at a user site. The resulting sequence data files can be transmitted to a cloud computing system where the sequence classification algorithm performs one or more operations of the methods described herein. At any step cloud computing system can transmit results of calculations back to the computer operated by the user.

Data can be transmitted electronically, e.g. over the Internet. Electronic communication can be, for example, over any communications network include, for example, a high-speed transmission network including, without limitation, Digital Subscriber Line (DSL), Cable Modem, Fiber, Wireless, Satellite and, Broadband over Powerlines (BPL). Information can be transmitted to a modem for transmission e.g. wireless or wired transmission, to a computer such as a desktop computer. Alternatively, reports can be transmitted to a mobile device. Reports may be accessible through a subscription program in which a user accesses a website which displays the report. Reports can be transmitted to an electronic device accessible by the user. This could be, for example, a personal computer, a laptop, a smart phone or a wearable device, e.g. worn on the wrist.

Systems can include non-transitory computer readable medium that can contain machine-executable code that, upon execution by a computer processor, implements a method of the present disclosure.

VII. Methods of Collecting Data, Communicating Results in Implementing Wellness/Therapeutic Interventions A subscription service can be provided in which a provider provides customers with one or more kits and/or one or more questionnaires for collecting subject data. This can include, for example, sending kits to a customer via a common carrier and receiving from the customer the kits including one or more biological samples from the subject. Questionnaires can be provided in physical form or over the Internet where questions are displayed on a webpage for a subject to answer and the provider receives, over the Internet, responses to questions.

The provider can process receive materials. This can include, for example, isolating and sequencing nucleic acids from biological samples provided by the subject and capture of responses to questionnaires in a computer database.

Inference models as described herein can be executed on subject data to produce predicted glycemic responses to food in the food ontology and/or further food/health recommendations.

Food recommendations can be provided to subjects through an Internet website. A website can be provided which can be accessed by a subject, e.g. a customer, through a password-protected portal. The website can include a clickable icon. Upon clicking the icon, the subject can receive personalized food recommendations. Such recommendations can be displayed on a webpage connected to the clickable icon. Subject can receive at an Internet connected server notification that personalized food recommendations for the subject are available.

Subjects receiving food and/or health recommendations can take interventions to improve wellness or health. Such interventions can include modifying diet to alter the diets macronutrient, micronutrient and/or supplement profile. Such modifications can include increasing absolute amounts and/or relative amounts of foods predicted to improve health or wellness, as well as decreasing absolute amounts and/or relative amounts of foods predicted to worsen health or wellness.

After wellness/therapeutic interventions are implemented, the effect of these interventions on the subject's phenotype and Omic profile can be remeasured such remeasurements can be used to generate updated recommendations as described herein.

EXAMPLES

Using metatranscriptomic technology and bioinformatics, as well as artificial intelligence algorithms, personalized food recommendations were developed. (Andrew Hatch et al., 2019, "A robust metatranscriptomic technology for population-scale studies of diet, gut microbiome, and human health" DOI: doi.org/10.31219/osf.io/8vd6x.) The recommendation engine uses glycemic response predictions to build a personalized base diet for each individual—a food with a lower predicted glycemic response is classified as Enjoy, and a food with higher predicted glycemic response is classified as Minimize. These foods are further stratified into Superfoods and Avoid foods based on other microbiome factors (taxa & genes (Kanehisa, M. and Goto, S.; KEGG: Kyoto Encyclopedia of Genes and Genomes. Nucleic Acids Res. 28, 27-30 (2000))) and phenotypes (obtained via questionnaires).

Study Design and Data Collection

To predict the glycemic response, it was sought to first understand exactly how individuals differ in their responses to specific foods as measured by blood glucose, and based on what factors. To collect this data systematically, a clinical study with 550 participants was performed, in which the following information was collected:

1) stool metatranscriptome (microbial taxa and functions)
2) phenotypes (based on a questionnaire)
3) continuous blood glucose measurements obtained every 15 minutes for 14 days
4) exact meal times and meal compositions
5) activity and sleep data provided by a wearable device.

The participants were provided with pre-designed breakfasts, snacks, and lunches for 14 days, and they recorded all meals during the study period. The provided meals captured a wide variety of real-world macro-nutrient proportions, as shown in FIG. 2. FIG. 3 shows data collected for a single participant over 2 days (out of 14). Using these methods, we collected data for about 25,000 meals, approximately half of which produced clean usable data from provided meals for which we knew the exact macronutrient content (carbs, fibers, proteins, and fats).

Model Development

The collected data showed that glycemic responses to meals depended not only on the macro nutrient content of the food, but also the attributes of the individual. FIG. 4 shows the glycemic response curves for 2 individuals for the same two food staples (banana and sprouted grain bread), which are almost the opposite of each other. Phenotypes and microbiome taxa and functions also have a strong influence.

Using machine learning, a model was devised to translate these complex blood glucose responses into simple binary ones (enjoy vs minimize) for each meal using all the available features of the input data. Labels (enjoy or minimize) were associated to glycemic responses based on what are acceptable versus suboptimal levels based on clinical experience.

Blood glucose response user/meal curves were clustered into similarly shaped curves and labeled using clinical expertise. (See FIG. 5.) This was an iterative process, so if the clinical expert felt a cluster was not homogeneous enough to assign a single label, the curves were re-clustered and the process repeated. Curves which appeared to be malfunctions of the readers were labeled as such and excluded.

We then built a machine learnt classification model using a combination of data attributes: (1) Meal information such as glycemic load, calories, weight of meal, carbohydrate proportion, protein proportion, fat proportion, etc. (2) Participant phenotypes such as age, weight, height, hip, waist, waist-to-hip, bmi (body mass Index), gender, etc., and (3) Microbiome data such as inflammatory and metabolic scores reported to users, as well as multiple aggregate scores associated with the expression of microbiome pathways.

Model Performance

Figure 6:
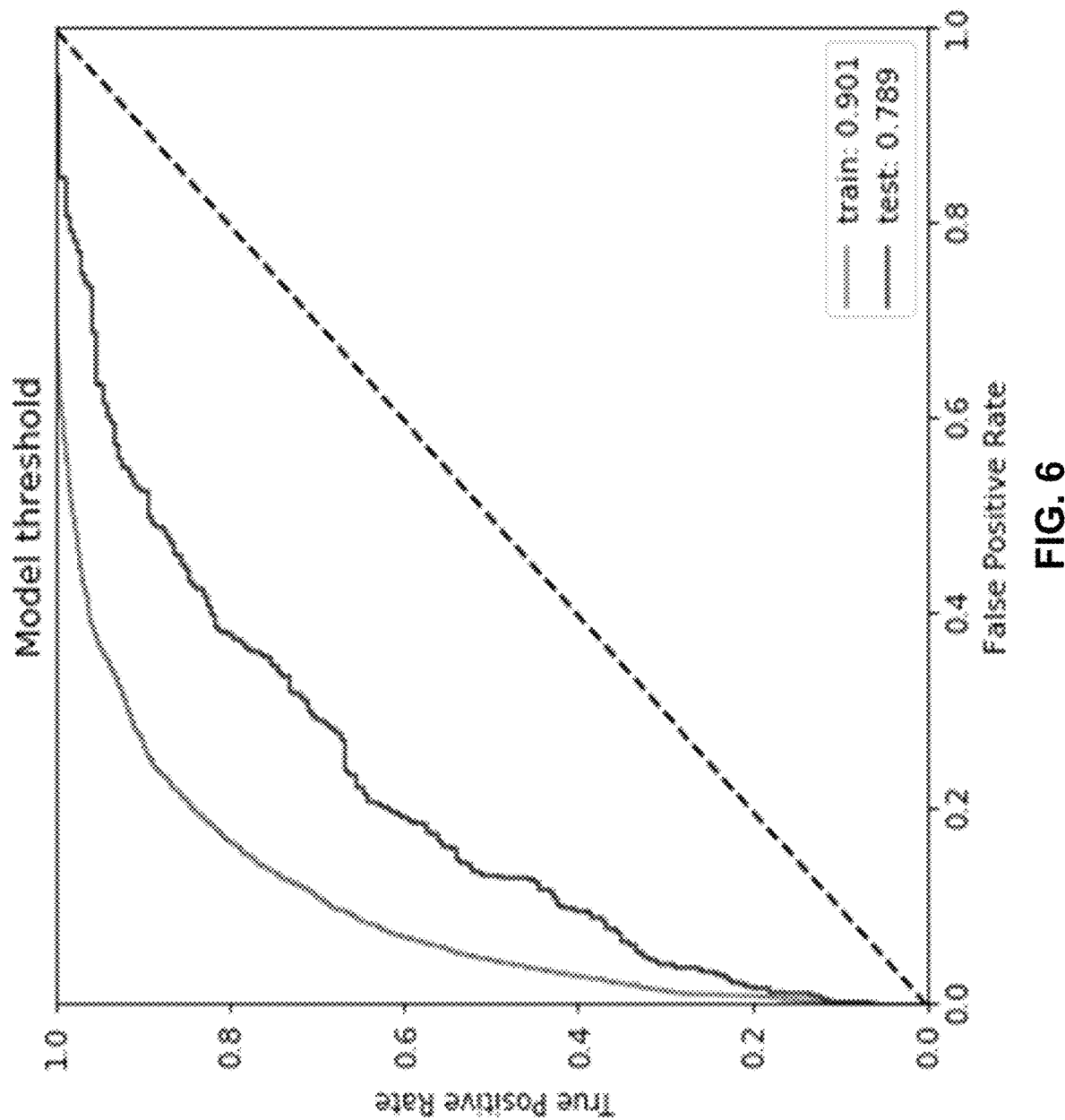
FIG. 6 shows receiver operating characteristic (ROC) curves for a model to predict glycemic response by an individual to a food as described herein. Performance of the model on the training set produced an area under the curve of 0.901, while performance of the model on the test set produced an area under the curve of 0.789.

The classification model described above performed at ~0.90 ROC AUC on a 10-fold cross-validation, and ~0.789 ROC AUC on unseen test data (see FIG. 6). Once the model was trained using study meals and study participants, we applied the same model to test subjects and a curated list of foods staples. We iteratively validated the output classifications to ensure that user staple predictions were sound from a clinical perspective.

Summary

A glycemic response predictor has been built using a robust methodology of data collection and modeling, and clinically validated to perform at a level of effectiveness considered commercially usable for a population of test subjects.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

What is claimed is:

1. A method of generating a glycemic response prediction model comprising:
   a) providing a dataset that comprises, for each of a plurality of subjects, data including:
      (i) omic data from the subject, comprising data about a microbiome of the subject;
      (ii) phenotypic data for a plurality of different phenotypic traits for the subject;
      (iii) meal data for each of a plurality of meals consumed by the subject, including a macronutrient profile for each meal; and
      (iv) glycemic response data for each subject indicating glycemic response by the subject to each of meals consumed; and
   b) training a learning algorithm to generate a model that infers a subject's glycemic response to a food or meal based on the subject's profile and the food or meal's macronutrient profile, wherein the model classifies the food or meal into a predicted glycemic response category among a plurality of predicted glycemic response categories comprising:
      (i) a lowest predicted glycemic response category,
      (ii) a highest predicted glycemic response category,
      (iii) a predicted glycemic response category below an average category but above the lowest predicted glycemic response category, and
      (iv) a predicted glycemic response category above the average category but below the highest predicted glycemic response category.

2. The method of claim 1, wherein the dataset comprises transcriptome data from a stool microbiome or blood transcriptome data.

3. The method of claim 1, wherein providing phenotypic data comprises providing a questionnaire to the subject and receiving from the subject answers to questions on the questionnaire.

4. The method of claim 1, wherein providing meal data comprises providing a food ontology comprising a macronutrient profile for each food in the food ontology.

5. The method of claim 1, wherein providing glycemic response data comprises providing each subject with one or a plurality of meals for consumption and, optionally, a schedule for consumption of the meals.

6. The method of claim 1, wherein providing glycemic response data comprises monitoring blood glucose levels in each subject during and after consumption of a meal.

7. The method of claim 1, wherein the omic data is abstracted to reflect one or more of:
   (A) microbiome taxa data for a plurality of microbes in the microbiome of the subject;
   (B) gene expression data comprising one or more individual genes or gene orthologs across taxa, for each of a plurality of genes in a microbiome of the subject; and
   (C) functional activity data on one or a plurality of different functional activities, comprising one or more of biochemical pathway activity, taxa group activity, and integrative functional activity.

8. A method of inferring the glycemic response by the subject to each of a plurality of foods, the method comprising:
   a) providing a test dataset comprising:
      (i) a subject profile comprising:
         (1) meta-transcriptomic data from a subject, comprising data from the subject's gut microbiome; and
         (2) phenotypic data for a plurality of different phenotypic traits for the subject;
      (ii) food data for each of a plurality of foods, including a macronutrient profile for each food; and
   b) executing a model of claim 4 on the dataset to infer the glycemic response by the subject to each of the foods.

9. A method comprising:
   a) providing a cohort of subjects;
   b) providing each subject in the cohort with questions about the subject's phenotype and receiving, from each subject, responses to the questions;
   c) providing each subject in the cohort with a kit for collecting a gut microbiome sample from the subject; receiving, from each subject, the kit comprising the gut microbiome sample; and determining omic data from each gut biological sample from each subject;
   d) providing each subject one or a plurality of meals to be consumed, each meal characterized by a macronutrient and, optionally, a micronutrient profile; and recording from each subject blood glucose levels including a span of time beginning before consumption of each of the one or more meal to at least any of 60 minutes, 70 minutes, 80 minutes, 90 minutes, 100 minutes, 110 minutes, 120 minutes, 130 minutes, 140 minutes, 150 minutes, 160 minutes, 170 minutes, or 180 minutes after consumption of the meal;
   e) providing a training dataset comprising data obtained at the providing (b), providing (c) and providing (d) or derived from such data; and
   f) training a learning algorithm on the training dataset to develop a model that predicts glycemic response of an individual subject to consumption of food based on the food's macronutrient profile, wherein the predicted glycemic response is selected from a plurality of predicted glycemic response categories comprising (i) a lowest predicted glycemic response category, (ii) a highest predicted glycemic response category, (iii) a predicted glycemic response category below an average category but above the lowest predicted glycemic response category, and (iv) a predicted glycemic response category above the average category but below a highest predicted glycemic response categories.

10. The method of claim 9, further comprising providing each subject with a kit for collecting a blood sample from the subject; receiving, from each subject, the kit comprising blood from the subject; and determining blood transcriptome data from the blood sample.

11. The method of claim 9, further comprising providing each subject with a kit for collecting a urine sample from the subject; receiving, from each subject, the kit comprising urine from the subject; and determining urine metabolome data from the urine sample.

12. A method comprising:
   a) training a learning algorithm on a training dataset to develop a model that predicts glycemic response of an individual to consumption of food based on the food's macronutrient profile, wherein:

the predicted glycemic response is selected from a plurality of predicted glycemic response categories comprising (i) a lowest predicted glycemic response category, (11) a highest predicted glycemic response category, (iii) a predicted glycemic response category below an average category but above the lowest predicted glycemic response category, and (iv) a predicted glycemic response category above the average category but below a highest predicted glycemic response categories;

b) selecting a subject for whom:
  (i) one or a plurality of foods is classified into the lowest predicted glycemic response category among the plurality of predicted glycemic response categories, wherein the lowest predicted glycemic response category comprises foods (e.g., classified as a superfood, and wherein the prediction takes into account phenotypic and omic data about the subject; or
  (ii) the one or a plurality of foods is classified into the highest predicted glycemic response category among the plurality of predicted glycemic response categories, wherein the highest predicted glycemic response category comprises foods (e.g., classified as an avoid food, and wherein the prediction takes into account phenotypic and omic data about the subject; and c) over a period of at least any of one day, one week, one month or one year,
  (i) increasing the amount of the one or a plurality of the foods classified into the lowest predicted glycemic response category in the diet of the subject compared with a time prior to the period, or
  (ii) decreasing the amount of the one or a plurality of the foods classified into the highest predicted glycemic response category in the diet of the subject compared with a time prior to the period.

13. The method of claim 12, comprising both
  (i) increasing the amount of one or a plurality of the foods classified into the lowest predicted glycemic response category in the diet of the subject and
  (ii) decreasing the amount of one or a plurality of the foods classified into the highest predicted glycemic response category in the diet of the subject.

14. The method of claim 12, wherein, for the subject:
  (i) one or a plurality of foods is classified into the predicted glycemic response category below the average category but above the lowest category, wherein the predicted glycemic response category below the average category but above the lowest category comprises foods (e.g., classified as an enjoy food, and wherein the prediction takes into account phenotypic and omic data about the subject; or
  (ii) the one or a plurality of foods is classified into the predicted glycemic response category above the average category but below the highest category, wherein the predicted glycemic response category above the average category but below the highest category comprises foods (e.g., classified as a minimize food, and wherein the prediction takes into account phenotypic and omic data about the subject; and the method further comprises:

c) over a period of at least any of one day, one week, one month or one year, (i) maintaining or increasing the amount of the one or a plurality of the foods classified in the below average category in the diet of the subject or (ii) maintaining or decreasing the amount of the one or a plurality of the foods classified in the above average category in the diet of the subject.

15. The method of claim 12, further comprising:
after selecting the subject, determining amounts of the one or more foods in the diet of the subject consumed over a period of at least any of one meal period, one day, one week or one month.

16. The method of claim 12, wherein one or more biological conditions in the subject is improved.

17. A system comprising:
(a) a computer comprising:
(i) a processor;
(ii) a memory, coupled to the processor; and
(iii) computer executable instructions comprising:
  instructions for obtaining a dataset that comprises, for each subject in a plurality of subjects, data including:
    (i) omic data from the subject,
    (ii) phenotypic data for a plurality of different phenotypic traits for the subject,
    (iii) meal data for each of a plurality of meals consumed by the subject, including a macronutrient profile for each meal, and
    (iv) glycemic response data for the subject indicating glycemic response by the subject to each of the plurality of meals consumed; and
  instructions for training a learning algorithm to generate a model that infers a subject's glycemic response to a food or meal based on the subject's profile and the food or meal's macronutrient profile, wherein the model classifies the food or meal into a predicted glycemic response category among a plurality of predicted glycemic response categories comprising:
    (i) a lowest predicted glycemic response category,
    (ii) a highest predicted glycemic response category,
    (iii) a predicted glycemic response category below an average category but above the lowest predicted glycemic response category, and
    (iv) a predicted glycemic response category above the average category but below the highest predicted glycemic response category.

* * * * *